US011896198B2

(12) United States Patent
Park

(10) Patent No.: US 11,896,198 B2
(45) Date of Patent: Feb. 13, 2024

(54) FLEXIBLE PORTION SHAPE ESTIMATING DEVICE AND ENDOSCOPE SYSTEM HAVING THE SAME

(71) Applicant: Yonho Park, Seoul (KR)

(72) Inventor: Yonho Park, Seoul (KR)

( * ) Notice: Subject to any disclaimer, the term of this patent is extended or adjusted under 35 U.S.C. 154(b) by 1007 days.

(21) Appl. No.: 16/333,639

(22) PCT Filed: May 15, 2018

(86) PCT No.: PCT/KR2018/005534
§ 371 (c)(1),
(2) Date: Mar. 15, 2019

(87) PCT Pub. No.: WO2018/212546
PCT Pub. Date: Nov. 22, 2018

(65) Prior Publication Data

US 2019/0208991 A1 Jul. 11, 2019

(30) Foreign Application Priority Data

May 16, 2017 (KR) ........................ 10-2017-0060691

(51) Int. Cl.
*A61B 1/00* (2006.01)
*A61B 1/005* (2006.01)
(Continued)

(52) U.S. Cl.
CPC .......... *A61B 1/00057* (2013.01); *A61B 1/005* (2013.01); *A61B 1/00006* (2013.01); *A61B 1/00045* (2013.01); *G01B 21/32* (2013.01); *G06T 7/0012* (2013.01); *A61B 2562/0247* (2013.01); *A61B 2562/0271* (2013.01)

(58) Field of Classification Search
CPC .............. A61B 1/00006; A61B 1/0005; A61B 1/00057; A61B 1/0011; A61B 1/00188; G02B 23/2423; G02B 7/04; G02B 7/28
See application file for complete search history.

(56) References Cited

U.S. PATENT DOCUMENTS 7,387,606 B2 * 6/2008 Weinberg ................. A61B 1/31 600/156
8,052,605 B2 * 11/2011 Muller ................. A61B 5/0062 600/463
(Continued)

FOREIGN PATENT DOCUMENTS

EP 2151184 A1 2/2010
EP 2229868 A1 9/2010
(Continued)

*Primary Examiner* — Timothy J Neal
*Assistant Examiner* — William B Chou
(74) *Attorney, Agent, or Firm* — Bridgeway IP Group, PLLC; Sang Ho Lee; Hyun Woo Shin

(57) ABSTRACT

Provided are a flexible portion shape estimating device and an endoscope system having the same. According to the present disclosure, the flexible portion shape estimating device includes a probe adapted to be inserted into a flexible portion and having a torque transmission wire transmitting a torque applied to one end thereof to other end thereof, and a rotation information measuring part coupled to other end of the probe to measure rotation information on the other end of the torque transmission wire.

9 Claims, 11 Drawing Sheets

(51) Int. Cl.
*G01B 21/32* (2006.01)
*G06T 7/00* (2017.01)

(56) References Cited

U.S. PATENT DOCUMENTS

| | | | | |
|---|---|---|---|---|
| 10,226,304 | B2* | 3/2019 | Iordachita | A61B 34/71 |
| 10,493,239 | B2* | 12/2019 | Hart | A61B 34/71 |
| 2007/0173694 | A1* | 7/2007 | Tsuji | A61B 1/0005 600/118 |
| 2007/0270650 | A1* | 11/2007 | Eno | A61B 5/06 600/117 |
| 2009/0093692 | A1* | 4/2009 | Hansma | A61B 5/103 433/98 |
| 2009/0227841 | A1* | 9/2009 | Miyako | A61B 1/0052 600/139 |
| 2010/0145150 | A1* | 6/2010 | Fukunaga | A61B 1/0011 600/140 |
| 2010/0160728 | A1* | 6/2010 | Yoshie | A61B 34/70 600/117 |
| 2011/0065994 | A1* | 3/2011 | Kudoh | A61B 1/0016 600/146 |
| 2011/0137122 | A1* | 6/2011 | Kawai | G05B 13/044 600/118 |
| 2011/0295063 | A1* | 12/2011 | Umemoto | A61B 1/0057 600/109 |
| 2013/0109919 | A1* | 5/2013 | Sugiyama | A61B 1/0016 600/117 |
| 2014/0236000 | A1* | 8/2014 | Kozuka | A61B 6/5235 600/424 |
| 2015/0054445 | A1* | 2/2015 | Kawai | A61B 1/00042 318/630 |
| 2015/0057575 | A1 | 2/2015 | Tsusaka et al. | |
| 2016/0073858 | A1* | 3/2016 | Sato | A61B 1/009 600/117 |
| 2017/0273542 | A1* | 9/2017 | Au | A61B 34/37 |

FOREIGN PATENT DOCUMENTS

| | | | |
|---|---|---|---|
| EP | 2599431 | A1 | 6/2013 |
| JP | 106-261858 | A | 9/1994 |
| JP | 2001-169998 | A | 6/2001 |
| JP | 2010-035768 | A | 2/2010 |
| JP | 2015-128589 | A | 7/2015 |
| JP | 2015-181495 | A | 10/2015 |
| JP | 2015-181643 | A | 10/2015 |
| WO | 2006/134881 | A1 | 12/2006 |
| WO | 2010/137373 | A1 | 12/2010 |
| WO | 2015/118773 | A1 | 8/2015 |

* cited by examiner

FLEXIBLE PORTION SHAPE ESTIMATING DEVICE AND ENDOSCOPE SYSTEM HAVING THE SAME

FIELD OF THE DISCLOSURE

The present disclosure relates to a flexible portion shape estimating device and an endoscope system having the same, particularly, to the flexible portion shape estimating device and an endoscope system having the same that are capable of estimating changes in the shape of a linear flexible portion like an endoscope, while the flexible portion is moving into an interior portion of a subject's body.

BACKGROUND OF THE DISCLOSURE

When a linear flexible portion like an endoscope is moving forward, resistance generally occurs in the moving direction of the flexible portion. As a result, the flexible portion is often bent or twisted. For example, the large intestine is long and not fixed to a specific portion of an abdominal cavity, but freely moves therein. Further, when a colonoscopy is carried out to check diseases of internal organs, a large intestine endoscope is passed through the lumen of the large intestine, and the front end periphery of the large intestine endoscope is usually monitored. However, at this time, the large intestine endoscope can be bent or twisted due to the resistance of the large intestine or tissues surrounding the large intestine.

When the large intestine endoscope is bent or twisted, it is impossible to move the large intestine endoscope forward, and therefore, the large intestine endoscope has to be maintained, neither bent nor twisted. Thus, a surgeon should recognize the changes in the shape of the large intestine endoscope to maintain the large intestine endoscope neither bent nor twisted. In other words, the surgeon has to check whether the large intestine endoscope is twisted in a clockwise, counterclockwise, or twisted at several places, not just in one place, so that he or she can easily perform manipulations for stretching out the large intestine endoscope.

In order to recognize changes in the shape of the flexible portion like an endoscope, in conventional practices, methods like using radiation such as fluoroscopy or radiography have been generally used. Under the conventional methods, however, both the patient receiving a colonoscopy and the surgeon performing the colonoscopy are exposed repeatedly to a large quantity of radiation, and furthermore, the price of the equipment is very high. Such high-priced equipment has been used only in limited places, and the above-mentioned problems can be only solved by surgeons with long experience, repeated trials and errors.

SUMMARY OF THE DISCLOSURE

The present disclosure has been presented to solve the above-identified problems, and the purpose of the present disclosure is to provide a flexible portion shape estimating device and an endoscope system having the capabilities of estimating changes in the shape of a linear flexible portion like an endoscope, while the flexible portion is moving into an interior of a subject's body.

To accomplish the above-identified object, according to the first aspect of the present disclosure, there is a provided flexible portion shape estimating device which includes a probe to be inserted into the flexible portion and having a torque transmission wire transmitting a torque applied to one end thereof to another end thereof, and a rotation information measuring part coupled to an end of the probe to measure rotation information on the other end of the torque transmission wire.

According to the present disclosure, the probe includes an outer tubular body having a wire channel formed in the interior thereof, and the torque transmission wire is inserted into the interior of the outer tubular body in such a manner as to be disposed in the wire channel, and one area of the torque transmission wire is fixedly coupled to the inner surface of the outer tubular body.

According to the present disclosure, in a preferred embodiment, the torque transmission wire is inserted toward the front end of the outer tubular body in such a manner as to be fixedly coupled to the outer tubular body around the front end of the outer tubular body.

According to the present disclosure, in a preferred embodiment, a lubricant is accommodated in the wire channel to reduce a frictional force between the inner surface of the outer tubular body and the torque transmission wire.

According to the present disclosure, in a preferred embodiment, the rotation information measuring part includes at least one of the torque sensor for measuring a torque on the other end of the torque transmission wire and a rotation angle sensor for measuring a rotation angle on the other end of the torque transmission wire.

According to the present disclosure, in a preferred embodiment, the probe includes a metal bar coupled to the other end of the torque transmission wire, and the rotation information measuring part measures either the rotation angle or the torque of the metal bar to obtain the rotation information on the other end of the torque transmission wire.

According to the present disclosure, in a preferred embodiment, the flexible portion shape estimating device further includes a controller for analyzing the rotation information on the other end of the torque transmission wire received from the rotation information measuring part to estimate a shape of the flexible portion into which the probe is inserted; and a display for receiving information on the estimated shape of the flexible portion from the controller to display the estimated shape of the flexible portion to a user.

According to the present disclosure, in a preferred embodiment, the device further includes a probe insertion length measuring part disposed around an inserting part of an endoscope treatment instrument to measure an insertion length of the probe, when the probe is inserted into the flexible portion after passing through the inserting part of the endoscope treatment instrument.

According to the present disclosure, in a preferred embodiment, the device further includes a controller for analyzing the rotation information on the other end of the torque transmission wire received from the rotation information measuring part and the probe insertion length received from the probe insertion length measuring part to estimate a shape of the flexible portion into which the probe is inserted, and a display for receiving the information on the estimated shape of the flexible portion from the controller to display the estimated shape of the flexible portion to a user.

According to the present disclosure, in a preferred embodiment, the device further includes a probe insertion length input part for receiving an insertion length of the probe when the probe is inserted into the flexible portion after passing through the inserting part of the endoscope treatment instrument from the user.

According to the present disclosure, in a preferred embodiment, the probe insertion length input part has a shape of a pedal and inputs the probe insertion length according to at least one of the number of times the pedal is stepped and a pedal stepping interval.

According to the present disclosure, in a preferred embodiment, the device further includes a controller for analyzing the rotation information on the other end of the torque transmission wire received from the rotation information measuring part and the probe insertion length received from the probe insertion length input part to estimate a shape of the flexible portion into which the probe is inserted, and a display for receiving information on the estimated shape of the flexible portion from the controller to display the estimated shape of the flexible portion to a user.

To accomplish the above-identified object, according to the second aspect of the present disclosure, there is an endoscope system having a flexible portion shape estimating device. The endoscope system includes a flexible portion configured to be bent by an external force and the flexible portion having a wire channel formed at the interior thereof, a torque transmission wire configured to be inserted into the interior of the flexible portion to be disposed in the wire channel to transmit a torque applied to one end thereof to other end thereof, and a rotation information measuring part coupled to the other end of the torque transmission wire to measure rotation information on the other end of the torque transmission wire.

According to the present disclosure, in a preferred embodiment, one area of the torque transmission wire is fixedly coupled to the inner surface of the flexible portion.

According to the present disclosure, in a preferred embodiment, the torque transmission wire is inserted toward a front end of the flexible portion in such a manner which is fixedly coupled to the flexible portion around the front end of the flexible portion.

According to the present disclosure, in a preferred embodiment, a lubricant is accommodated in the wire channel to reduce a frictional force between the inner surface of the flexible portion and the torque transmission wire.

According to the present disclosure, in a preferred embodiment, the rotation information measuring part includes at least one of the torque sensors for measuring a torque on the other end of the torque transmission wire and a rotation angle sensor for measuring the rotation angle on the other end of the torque transmission wire.

According to the present disclosure, in a preferred embodiment, the endoscope system further includes a metal bar coupled to the other end of the torque transmission wire, and the rotation information measuring part measures the rotation angle and the torque of the metal bar to measure the rotation information on the other end of the torque transmission wire.

According to the present disclosure, in a preferred embodiment, the endoscope system further includes a controller for analyzing the rotation information on the other end of the torque transmission wire received from the rotation information measuring part to estimate the shape of the flexible portion, and a display for receiving information on the estimated shape of the flexible portion from the controller to display the estimated shape of the flexible portion to a user.

According to the present disclosure, in a preferred embodiment, the endoscope system further includes an endoscope insertion length measuring part for measuring the insertion length of an endoscope inserting part having the flexible portion when the endoscope inserting part is inserted into the patient's body.

According to the present disclosure, in a preferred embodiment, the endoscope system further includes a controller for analyzing the rotation information on the other end of the torque transmission wire received from the rotation information measuring part and the endoscope insertion length received from the endoscope insertion length measuring part to estimate a shape of the flexible portion, and a display for receiving information on the estimated shape of the flexible portion from the controller to display the estimated shape of the flexible portion to the user.

According to the present disclosure, in a preferred embodiment, the endoscope system further includes an endoscope insertion length input part for receiving an endoscope insertion length as an insertion length of an endoscope inserting part having the flexible portion, when the endoscope inserting part is inserted into a patient's body from the user.

According to the present disclosure, in a preferred embodiment, the endoscope insertion length input part has a shape of a pedal and inputs the endoscope insertion length according to at least one of the number of times the pedal is stepped and the pedal stepping interval.

According to the present disclosure, in a preferred embodiment, the endoscope system further includes a controller for analyzing the rotation information on the other end of the torque transmission wire received from the rotation information measuring part and the endoscope insertion length received from the endoscope insertion length input part to estimate a shape of the flexible portion, and a display part for receiving information on the estimated shape of the flexible portion from the controller to display the estimated shape of the flexible portion to the user.

According to the present disclosure, the flexible portion shape estimating device and the endoscope system having the same are capable of estimating changes in the shape of the linear flexible portion like an endoscope without using radiation, when the flexible portion is moving into the interior portion of a subject's body.

DETAILED DESCRIPTION

Figure 1:
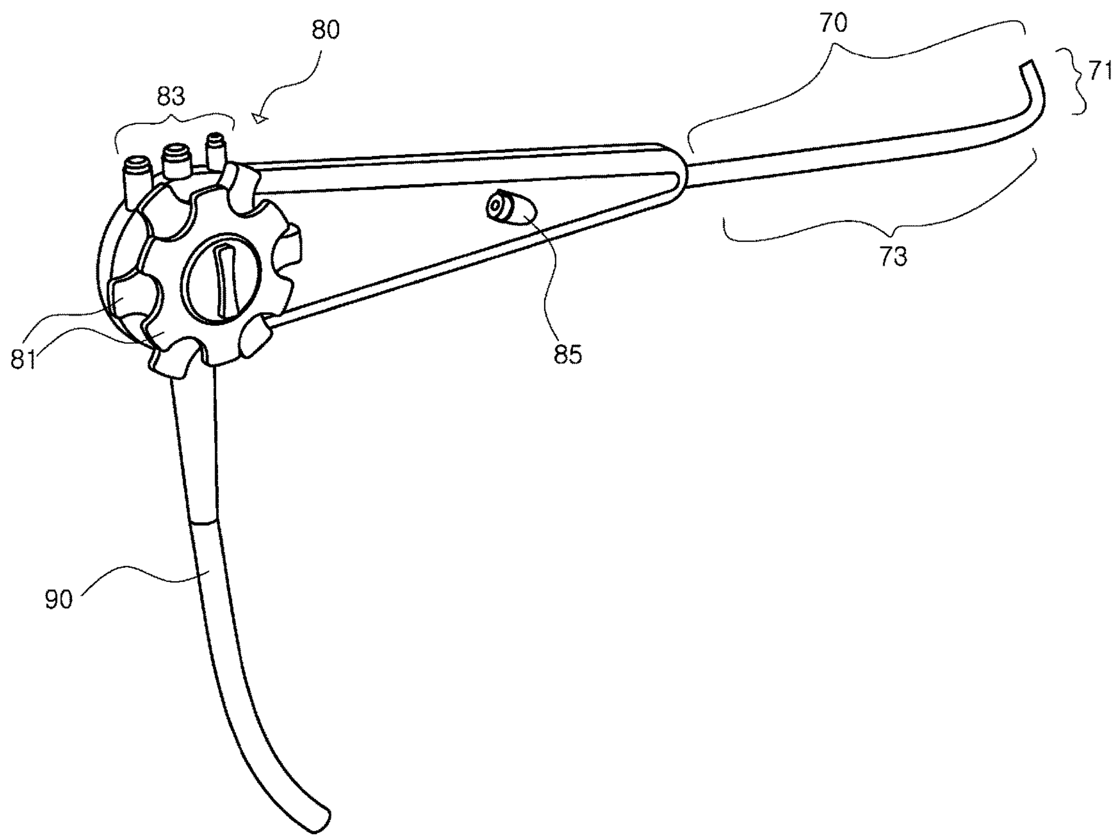
FIG. 1 is a perspective view showing an endoscope device to which a flexible portion shape estimating device according to a first embodiment of the present disclosure is applied.

Hereinafter, the present disclosure will be explained in detail with references to the attached drawings. Before the present disclosure is disclosed and described, it is to be understood that the corresponding parts in the embodiments of the present disclosure are indicated by corresponding reference numerals and the repeated explanation on the corresponding parts will be avoided. If it is determined that the detailed explanation about well-known technology related to the present disclosure makes the scope of the present disclosure not clear, the explanation will be avoided for the brevity of the description. Also, the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present disclosure in virtually any appropriately detailed structure.

In the description, when it is said that one element is described as being "connected" or "coupled" to another element, one element may be directly connected or coupled to the other element, but it should be understood that another element may be present between the two elements. In the description, furthermore, when it is said that one portion is described as "includes" in any component, one element further may include other components unless no specific description is suggested.

FIG. 1 is a perspective view showing an endoscope device to which a flexible portion shape estimating device according to the first embodiment of the present disclosure is applied. As shown in FIG. 1, the endoscope device includes an endoscope inserting part 70, an endoscope operating part 80, and a universal cord 90.

The endoscope inserting part 70 is coupled to one area of the endoscope operating part 80 and is also inserted into the subject's body. The endoscope inserting part 70 includes a freely bendable portion 71 and a flexible portion 73 having flexibility in such a manner as it can be easily bent and returned to its original shape by means of an external force. Even if not shown in FIG. 1, parts like an observing window, a light window, a treatment instrument insertion channel opening, an air transmitting nozzle, and a water transmitting nozzle may be disposed on one end of the bendable portion 71.

The endoscope operating part 80 is disposed between the endoscope inserting part 70 and the universal cord 90. The endoscope operating part 80 is held by a surgeon to operate the endoscope device. The endoscope operating part 80 includes bent operating levers 81 and an operating switch part 83, and furthermore, it includes an endoscope treatment instrument inserting part 85 disposed on a side surface thereof.

The bent operating levers 81 serve to control the bending operation of the bendable portion 71 of the endoscope inserting part 70. The bent operating levers 81 operate by the surgeon to allow the bendable portion 71 to be bent or stretched in any given direction. The operating switch part 83 may include a plurality of switches. The respective switches are adapted to control freeze and release of an endoscope image or to perform air transmission, water transmission, and suction through the endoscope inserting part 70. Air or water is supplied or sucked to or from a patient's body by means of the surgeon's manipulation of the operating switch part 83. Furthermore, the endoscope image is stopped or reproduced through the operating switch part 83.

As shown in FIG. 1, the endoscope treatment instrument inserting part 85 is disposed on one area of the endoscope operating part 80. The endoscope treatment instrument inserting part 85 has a through hole into which an endoscope treatment instrument like forceps is inserted and also communicates with an endoscope treatment instrument channel 74 (See FIG. 5) formed in an interior of the endoscope inserting part 70.

The universal cord 90 is coupled to one area of the endoscope operating part 80 and includes a transmission cord for a camera or a light source unit of the endoscope, an air transmission tube, a water transmission tube, and a suction tube, disposed in the interior thereof. The transmission cord, the air transmission tube, the water transmission tube, and the suction tube pass through the interior of the endoscope operating part 80 in such a manner which is extended to the endoscope inserting part 70. The endoscope inserting part 70 has a channel formed to pass the transmission cord, air transmission tube, water transmission tube, and suction tube. Even if not shown in FIG. 1, the other end of the universal cord 90 is connected to an endoscope monitoring device 55 (See FIG. 10) for monitoring the electromagnetic state of the endoscope system.

The endoscope device as shown in FIG. 1 is exemplary, and therefore, the endoscope device of the flexible portion shape estimating device according to the present disclosure is applied can be freely changed.

Figure 2:
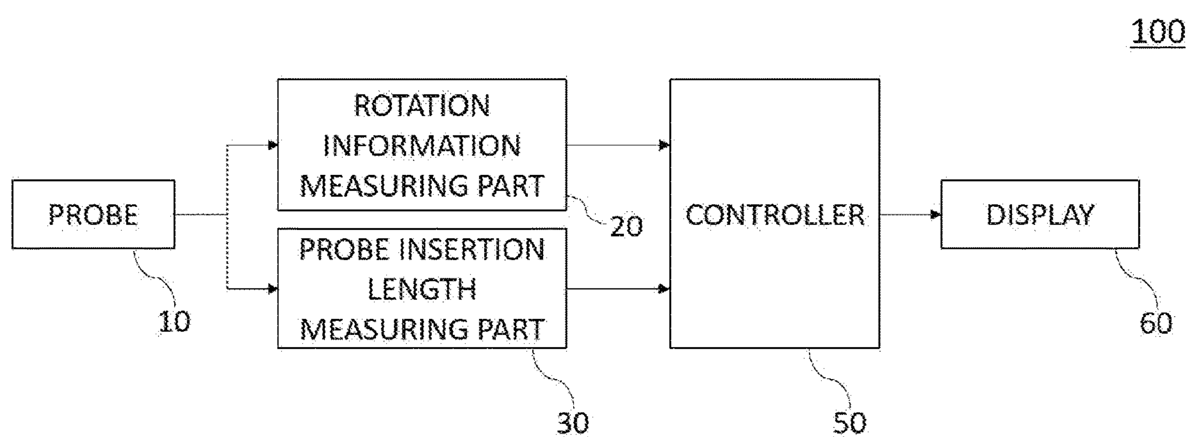
FIG. 2 is a block diagram showing a flexible portion shape estimating device according to the first embodiment of the present disclosure.

FIG. 2 is a block diagram showing a flexible portion shape estimating device according to the first embodiment of the present disclosure. As shown in FIG. 2, the flexible portion shape estimating device 100 according to the first embodiment of the present disclosure includes a probe 10 and a rotation information measuring part 20. According to the present disclosure, further, the flexible portion shape estimating device 100 includes a probe insertion length measuring part 30, a controller 50 and a display 60.

The probe 10 is inserted into the flexible portion 73 of the endoscope device as shown in FIG. 1. The probe 10 includes a torque transmission wire 13 (See FIG. 3) for transmitting a torque applied to one end thereof to the other end thereof. The torque transmission wire 13 is made of a stainless steel material having given stiffness and transmits the torque applied to one end thereof to the other end thereof at almost the same ratio of 1:1. Even in a state where the torque transmission wire 13 is bent, the torque transmission ratio is close to 1:1. For example, a torque transmission wire made by Asahi Intecc Co., Ltd. is widely known on the market.

The probe 10 further includes an outer tubular body 11 (See FIG. 3) having a wire channel 15 (See FIG. 3) formed in the interior thereof. The torque transmission wire 13 is disposed in the wire channel 15 of the interior of the outer tubular body 11. A detailed explanation on the shape of the probe 10 will be given later with reference to FIGS. 3 to 6.

The rotation information measuring part 20 is coupled to the other end of the probe 10 to measure rotation information on the other end of the torque transmission wire 13. The other end of the torque transmission wire 13, which is disposed in the wire channel 15 of the interior of the outer tubular body 11, is connected to the rotation information measuring part 20. For example, the rotation information on the other end of the torque transmission wire 13 includes information capable of recognizing a degree of rotation on the other end of the torque transmission wire 13, such as a torque or rotation angle on the other end of the torque transmission wire 13.

The rotation information measuring part 20 includes at least one of torque sensors (not shown) for measuring the torque on the other end of the torque transmission wire 13 and a rotation angle sensor (not shown) for measuring the rotation angle on the other end of the torque transmission wire 13. The torque sensor is a sensor for measuring a torque by using a Surface Acoustic Wave (SAW) technology using surface wavelengths, an Embedded Magnetic Domain (EMD) technology for measuring changes in a magnetic field generated by rotation, and an optical sensor technology using a laser diode and a photodiode. The rotation angle sensor measures the rotation angle by means of non-contacting using a Hall sensor and a magnet. In addition, the torque sensor and the rotation angle sensor may be freely changed to various sensors capable of measuring the torque and rotation angle of the torque transmission wire 13.

The probe insertion length measuring part 30 is disposed around the endoscope treatment instrument inserting part 85. The probe insertion length measuring part 30 measures a probe insertion length which is the inserted length of the probe 10 into the flexible portion 73 after passing through the inserting part 85 of the endoscope treatment instrument. If the insertion length of the probe 10 into the flexible portion 73 is measured, the controller 50 can accurately estimate the current shape of the flexible portion 73. The probe insertion length measuring part 30 can be implemented by a rotation type roller, a laser, and an ultrasonic wave. If the probe insertion length measuring part 30 is the rotation type roller, for example, the rotation type roller comes into contact with the probe 10 at the time when the probe 10 is inserted into the flexible portion 73 through the endoscope treatment instrument inserting part 85 and thus rotates, so that through the number of rotation times of the rotation type roller and the peripheral length of the rotation type roller, the insertion length of the probe 10 into the flexible portion 73 can be measured. According to the present disclosure, if the probe 10 moves backward from the flexible portion 73, the probe insertion length measured by the probe insertion length measuring part 30 is decreased. If the probe insertion length measuring part 30 is the rotation type roller, the probe insertion length can be increased or decreased according to the rotation direction of the rotation type roller.

The controller 50 analyzes the rotation information on the other end of the torque transmission wire 13 received from the rotation information measuring part 20 and the probe insertion length received from the probe insertion length measuring part 30 to estimate the shape of the flexible portion 73 into which the probe 10 is inserted. The controller 50 analyzes at least one of the torque and the rotation angle on the other end of the torque transmission wire 13 to obtain the rotation information on the other end of the torque transmission wire 13.

According to the present disclosure, the controller 50 may analyze the rotation information on the other end of the torque transmission wire 13 received from the rotation information measuring part 20 to estimate the shape of the flexible portion 73 into which the probe 10 is inserted. For example, the probe insertion length measuring part 30 does not exist so that no probe insertion length is provided, and in this case, the controller 50 sequentially displays, on the display 60, the rotation information on the other end of the torque transmission wire 13 according to time.

The display 60 receives the information on the estimated shape of the flexible portion 73 from the controller 50 and displays the estimated shape of the flexible portion 73 to the user. For example, the display 60 displays the estimated shape of the flexible portion 73 as a two-dimensional or three-dimensional image. According to the present disclosure, the display 60 may display a graph wherein the probe insertion length is indicated by an axis X and the rotation angle on the other end of the torque transmission wire 13 by an axis Y, or provide only the information on the torque or rotation angle on the other end of the torque transmission wire 13.

Figure 3:
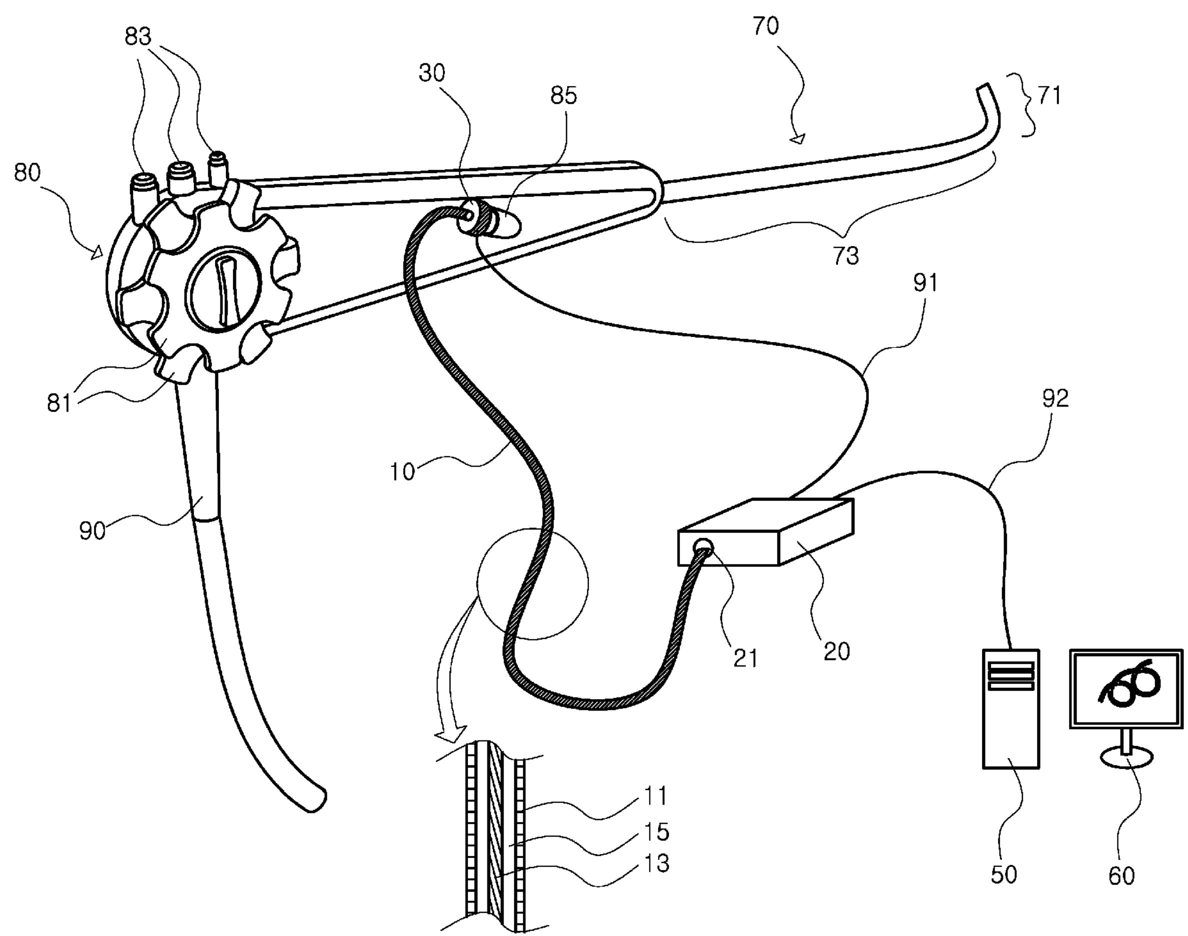
FIG. 3 is a perspective view showing a usage of the flexible portion shape estimating device according to the first embodiment of the present disclosure.

FIG. 3 is a perspective view showing a in use state of the flexible portion shape estimating device according to the first embodiment of the present disclosure. The flexible portion shape estimating device 100 as shown in FIG. 2 may be implemented as shown in FIG. 3. As shown in FIG. 3, the flexible portion shape estimating device 100 according to the first embodiment of the present disclosure includes the probe 10, the rotation information measuring part 20, the probe insertion length measuring part 30, the controller 50 and the display 60.

The probe 10 has a shape of a tubular body in such a manner as to be inserted into the endoscope treatment instrument inserting part 85. Also, the probe 10 is connected to the rotation information measuring part 20. The probe 10 includes the outer tubular body 11, the torque transmission wire 13, and the wire channel 15. The outer tubular body 11 has a shape of a tubular body and includes the wire channel 15 formed in the interior thereof.

The torque transmission wire 13 is inserted into the outer tubular body 11 and is then disposed in the wire channel 15. One area of the torque transmission wire 13 is fixedly coupled to the inner surface of the outer tubular body 11. The torque transmission wire 13 is fixed to a given portion of the outer tubular body 11 inside the outer tubular body 11. For example, the torque transmission wire 13 is inserted toward the front end of the outer tubular body 11 and is then fixedly coupled to the outer tubular body 11 around the front end of the outer tubular body 11. If the probe 10 is inserted into the endoscope inserting part 70 through the endoscope treatment instrument inserting part 85 and then moves to the bendable portion 71, accordingly, the torque generated when the probe 10 rotates according to the bent or twisted shape of the endoscope inserting part 70 is transmitted to the rotation information measuring part 20 through the torque transmission wire 13. According to the present disclosure, the probe 10 may include only the torque transmission wire 13, without having the outer tubular body 11.

The rotation information measuring part 20 is coupled to the other end of the probe 10 to measure the rotation information on the other end of the torque transmission wire 13. The rotation information measuring part 20 is connected to the probe 10 through a probe coupling part 21. For example, the other end of the torque transmission wire 13 of the probe 10 passes through the probe coupling part 21 and is thus disposed inside the rotation information measuring part 20. The other end of the torque transmission wire 13 is disposed on a position adjacent to the torque sensor or the rotation angle sensor of the rotation information measuring part 20.

The rotation information measuring part 20 measures the torque generated by the torque transmission wire 13 or measures the rotation angle of the torque transmission wire 13 generated from the torque. The rotation information measuring part 20 is connected to the probe insertion length measuring part 30 through a communication line 91 to transmit and receive data to and from each other. The rotation information measuring part 20 and the controller 50 are connected to each other by means of a communication line 92 to transmit and receive data to and from each other.

The probe insertion length measuring part 30 is mounted onto the endoscope treatment instrument inserting part 85. The probe insertion length measuring part 30 measures the probe insertion length as the insertion length of the probe 10 into the flexible portion 73 after passing through the endoscope treatment instrument inserting part 85. The probe insertion length is the moving distance of the probe 10 toward the bendable portion 71 after passing through the inserting part 85 of the endoscope treatment instrument. As shown in FIG. 3, the probe insertion length measuring part 30 has a through hole formed to pass the probe 10 therethrough and a rotation type roller disposed around the through hole to measure the probe insertion length. The probe 10 is inserted into the endoscope treatment instrument channel 74 (See FIG. 5) formed in the interior of the endoscope inserting part 70 through the endoscope treatment instrument inserting part 85.

The controller 50 analyzes the rotation information on the other end of the torque transmission wire 13 received from the rotation information measuring part 20 and the probe insertion length received from the probe insertion length measuring part 30 to estimate the shape of the flexible portion 73 into which the probe 10 is inserted. The controller 50 analyzes at least one of the torque and the rotation angle on the other end of the torque transmission wire 13 to obtain the rotation information on the other end of the torque transmission wire 13.

The controller 50 allows the rotation information on the other end of the torque transmission wire 13 measured during the probe 10 is inserted into the flexible portion 73 to correspond respectively to the probe insertion length received from the probe insertion length measuring part 30. As a result, the controller 50 extracts the rotation information corresponding to each point of the probe 10 and estimates the whole shape of the probe 10 from the extracted rotation information. As the probe 10 passes through the flexible portion 73, the shape of the probe 10 can be estimated as the shape of the flexible portion 73. As shown in FIG. 3, the controller 50 is a body of a PC terminal serving as an endoscope shape display device and includes a CPU capable of performing data input/output and data processing.

The display 60 receives the information on the estimated shape of the flexible portion 73 from the controller 50 and displays the estimated shape of the flexible portion 73 to the user. The display 60 displays screens according to the display signals received from the controller 50 and provides the screens to the user. The display 60 is a monitor connected to the PC terminal serving as the endoscope shape display device. The display 60 is disposed on the outer surface of the controller 50 or connected to an external device. As known to a person having ordinary skill in the art, the display 60 can be made with liquid crystal diode (LCD), light emitting diode (LED), organic light emitting diode (OLED), and other displays.

While the endoscope inserting part 70 is inserted and moved in the subject's body, as shown in FIG. 3, the flexible portion shape estimating device 100 according to the first embodiment of the present disclosure allows a major axis of the flexible portion 73 to be bent like a spring coil if resistance occurs in the moving direction to the flexible portion 73. A portion of elastic energy generated from the resistance generates a torque around the major axis of the flexible portion 73, and through the generation of the torque, the flexible portion 73 rotates around the major axis.

After that, if the probe 10 moves to the interior of the flexible portion 73 through the endoscope treatment instrument channel 74 inside the flexible portion 73, the probe 10 rotates according to the twisted shape of the flexible portion 73, so that a torque is generated from the front-end periphery of the torque transmission wire 13. The torque generated from the front-end periphery of the torque transmission wire 13 is transmitted to the rotation information measuring part 20. When the probe 10 moves to the interior of the flexible portion 73 through the endoscope treatment instrument inserting part 85, the probe insertion length measuring part 30 connected to the probe 10 measures the moving distance of the probe 10 to the interior of the flexible portion 73.

The rotation information of the torque transmission wire 13 obtained from the rotation of the torque transmission wire 13 and the moving distance of the probe 10 toward the front-end periphery of the flexible portion 73 in the interior of the flexible portion 73 have a consistent relationship with the changes in the shape of the flexible portion 73. In detail, as the torque change transmitted to the torque transmission wire 13 per a unit moving distance of the probe 10 in the interior of the flexible portion 73 or a rotation angle change by the rotation of the torque transmission wire 13 per the unit moving distance of the probe 10 in the interior of the flexible portion 73 is increased, a degree of twist of the flexible portion 73 is increased. Through the torque change or the rotation angle change, accordingly, the controller 50 estimates the changes in the shape of the flexible portion 73 caused by the bending or twisting of the flexible portion 73.

On the other hand, as shown in FIG. 3, the rotation information measuring part 20, the controller 50, and the display 60 are physically separated from each other, but of course, they may be integrated to one body. Further, the communication lines 91 and 92 may be changed or removed, and according to the present disclosure, the rotation information measuring part 20, the probe insertion length measuring part 30, and the controller 50 can transmit and receive data to and from each other by means of wireless communication.

According to the present disclosure, on the other hand, the probe 10 may further include a metal bar (not shown) coupled to the other end of the torque transmission wire 13. The metal bar is connected to the rotation information measuring part 20, and the rotation information measuring part 20 measures at least one of the rotation angles and the torque of the metal bar to measure the rotation information on the other end of the torque transmission wire 13. If it is difficult to directly measure the rotation information on the other end of the torque transmission wire 13, the rotation information of the metal bar coupled to the other end of the torque transmission wire 13 is measured so that the rotation information on the other end of the torque transmission wire 13 can be indirectly measured.

Figure 4:
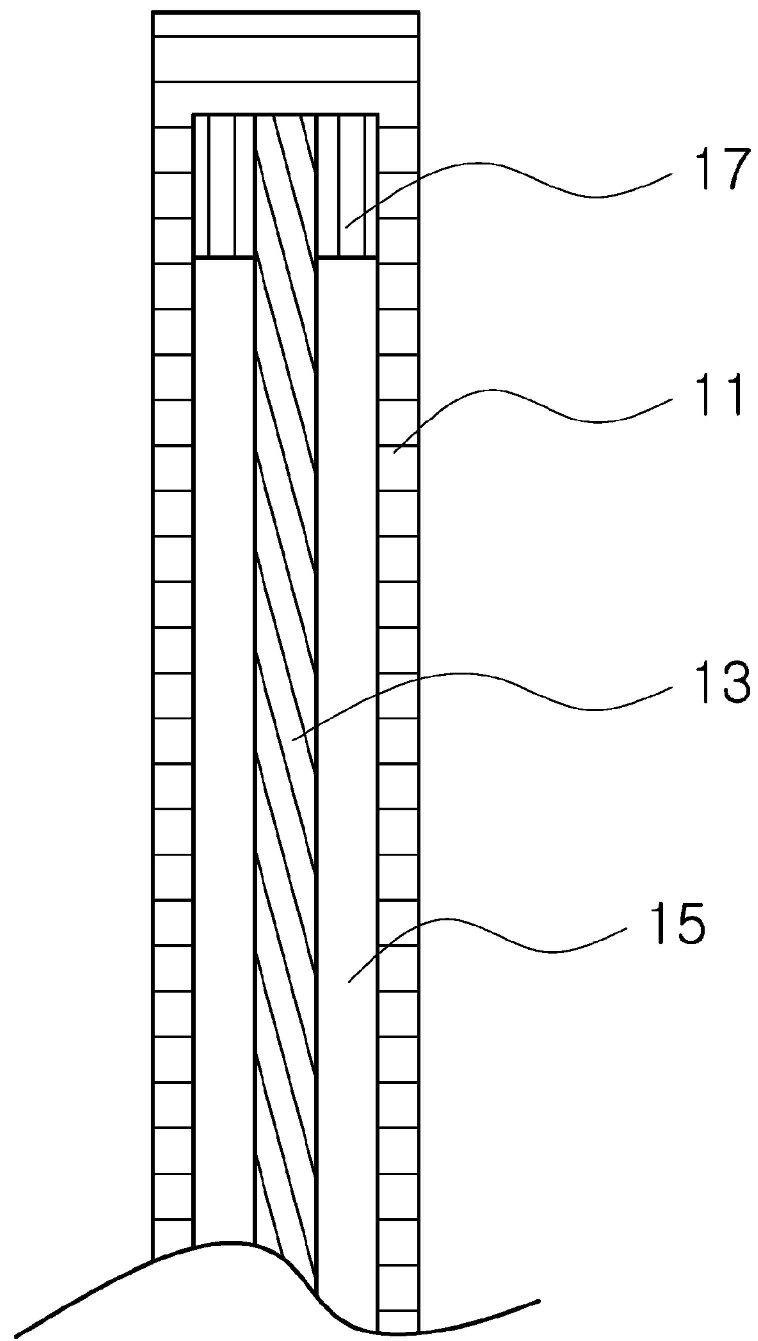
FIG. 4 is a sectional view showing a probe of the flexible portion shape estimating device according to the first embodiment of the present disclosure.

FIG. 4 is a sectional view showing the probe of the flexible portion shape estimating device according to the first embodiment of the present disclosure. In detail, FIG. 4 shows the front-end periphery of the probe 10 of the flexible portion shape estimating device 100 according to the first embodiment of the present disclosure.

As shown in FIG. 4, the probe 10 of the flexible portion shape estimating device 100 according to the first embodiment of the present disclosure includes the outer tubular body 11, the torque transmission wire 13, the wire channel 15 and a wire fixing member 17. As mentioned above, the probe 10 passes through the endoscope treatment instrument inserting part 85 and is then inserted into the endoscope treatment instrument channel 74 of the endoscope inserting part 70.

The outer tubular body 11 includes the wire channel 15 formed at the interior thereof. For example, the wire channel 15 is empty.

The torque transmission wire 13 is inserted into the outer tubular body 11 and is then disposed in the wire channel 15. One area of the torque transmission wire 13 is fixedly coupled to the inner surface of the outer tubular body 11. The torque transmission wire 13 is inserted toward the front-end periphery of the outer tubular body 11 and is then fixedly coupled to the outer tubular body 11 around the front end of the outer tubular body 11.

As shown in FIG. 4, the wire fixing member 17 is formed along the front-end inner periphery of the outer tubular body 11, and by means of the wire fixing member 17, the torque transmission wire 13 is fixed to the front-end periphery of the outer tubular body 11. Only if the wire fixing member 17 fixedly couples with the torque transmission wire 13 to the front-end periphery of the outer tubular body 11, it can be freely changed to various coupling means.

According to the present disclosure, a lubricant may be accommodated in the wire channel 15 to reduce a frictional force between the inner surface of the outer tubular body 11 and the torque transmission wire 13. Through the lubricant, the torque transmission wire 13 does not come into contact with the inner surface of the outer tubular body 11, and otherwise, the frictional force between the inner surface of the outer tubular body 11 and the torque transmission wire 13 is reduced, so that the torque generated from one end of the torque transmission wire 13 is accurately transmitted to the other end of the torque transmission wire 13, without any loss in the middle of the torque transmission wire 13.

According to the present disclosure, further, the material for reducing a frictional force may be coated onto the outer peripheral surface of the torque transmission wire 13 to reduce the frictional force between the inner peripheral surface of the outer tubular body 11 and the torque transmission wire 13. For example, the material for reducing the frictional force is polytetrafluoroethylene (PTFE), and of course, it may be freely changed to various materials.

Figure 5:
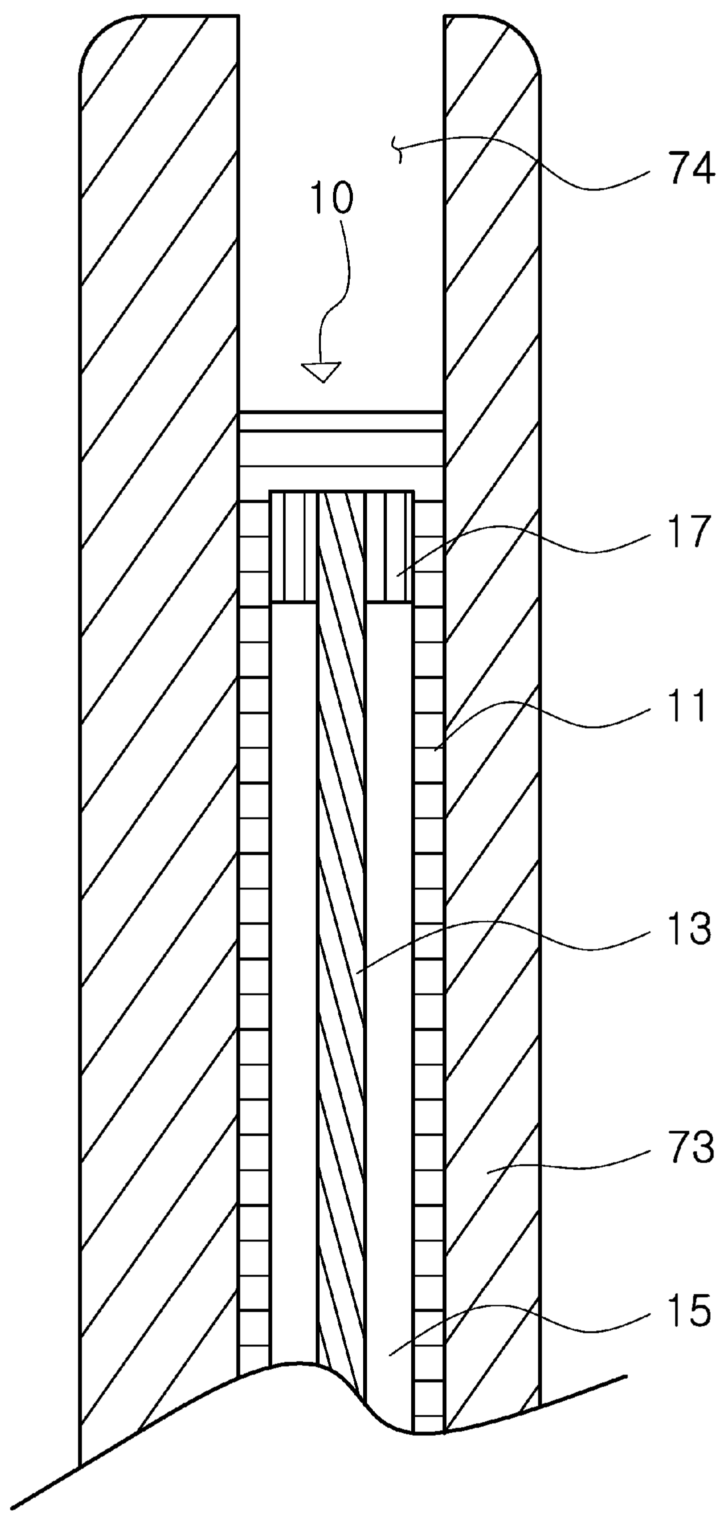
FIG. 5 is a sectional view showing a state where the probe of the flexible portion shape estimating device according to the first embodiment of the present disclosure is inserted into a flexible portion.

FIG. 5 is a sectional view showing a state where the probe of the flexible portion shape estimating device according to the first embodiment of the present disclosure is inserted into the flexible portion.

As shown in FIG. 5, the endoscope treatment instrument channel 74 is formed inside the flexible portion 73 of the endoscope inserting part 70. As shown, the front end of the endoscope treatment instrument channel 74 communicates with the outside. Even if not shown in FIG. 5, the bendable portion 71 as shown in FIG. 3 is formed on one end of the flexible portion 73.

The probe 10 is inserted into the endoscope treatment instrument channel 74. As described above with reference to FIG. 4, the probe 10 includes the outer tubular body 11, the torque transmission wire 13, the wire channel 15 and the wire fixing member 17.

Figure 6:
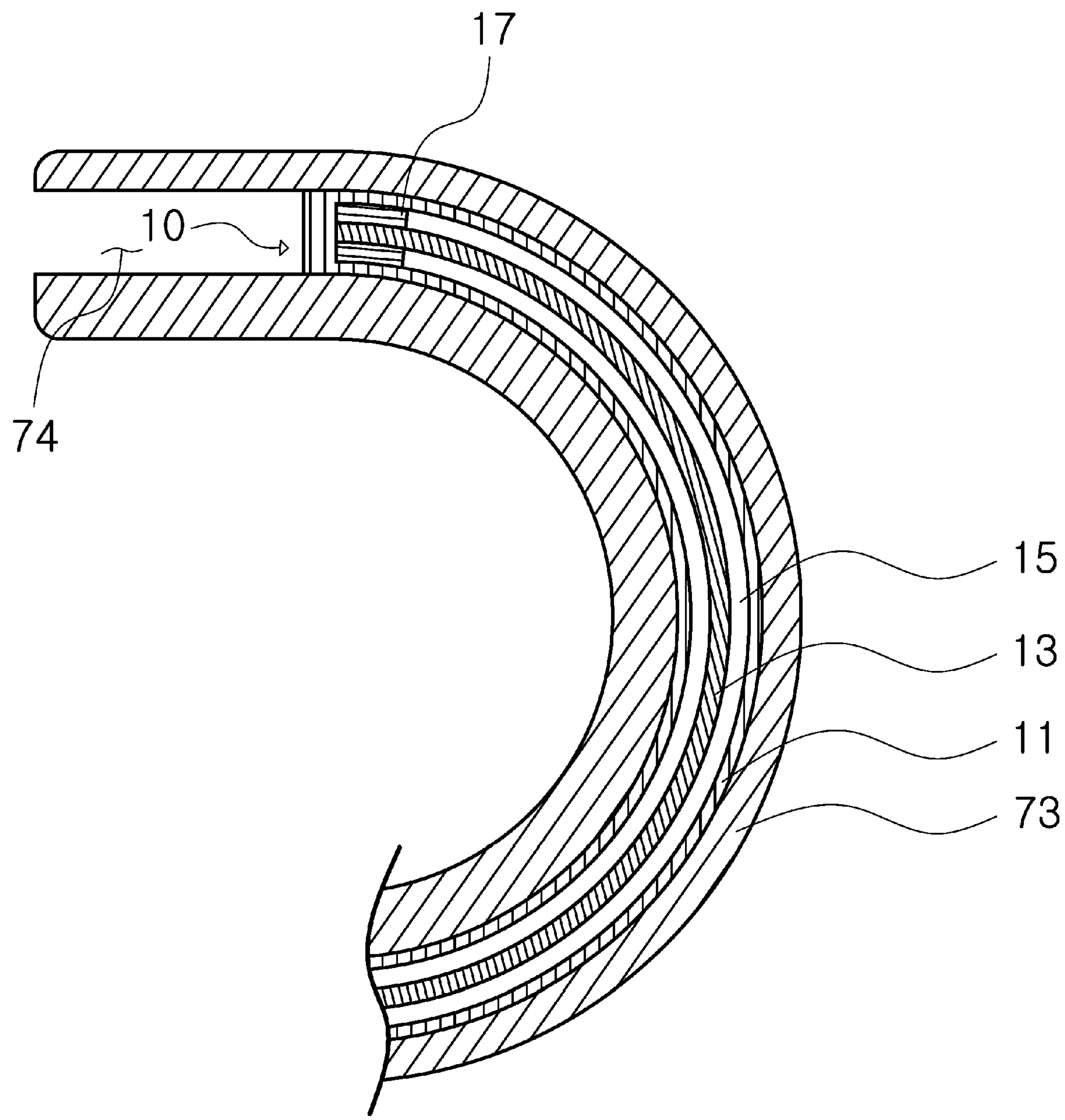
FIG. 6 is a sectional view showing a bent state of the flexible portion into which the probe of the flexible portion shape estimating device according to the first embodiment of the present disclosure is inserted.

FIG. 6 is a sectional view showing a bent state of the flexible portion into which the probe of the flexible portion shape estimating device according to the first embodiment of the present disclosure is inserted. FIG. 6 shows a state where the probe 10 is inserted into the bent flexible portion 73.

If the probe 10 is bent or twisted as it passes through the endoscope treatment instrument channel 74 inside the flexible portion 73, the rotation force generated from the front-end periphery of the probe 10 around the wire fixing member 17 is transmitted to the rotation information measuring part 20 through the torque transmission wire 13.

The controller 50 analyzes the rotation information on the other end of the torque transmission wire 13 received from the rotation information measuring part 20 and the probe insertion length received from the probe insertion length measuring part 30 to estimate the shape of the flexible portion 73 into which the probe 10 is inserted. The display 60 receives the information on the estimated shape of the flexible portion 73 from the controller 50 and displays the estimated shape of the flexible portion 73 to the user.

Figure 7:
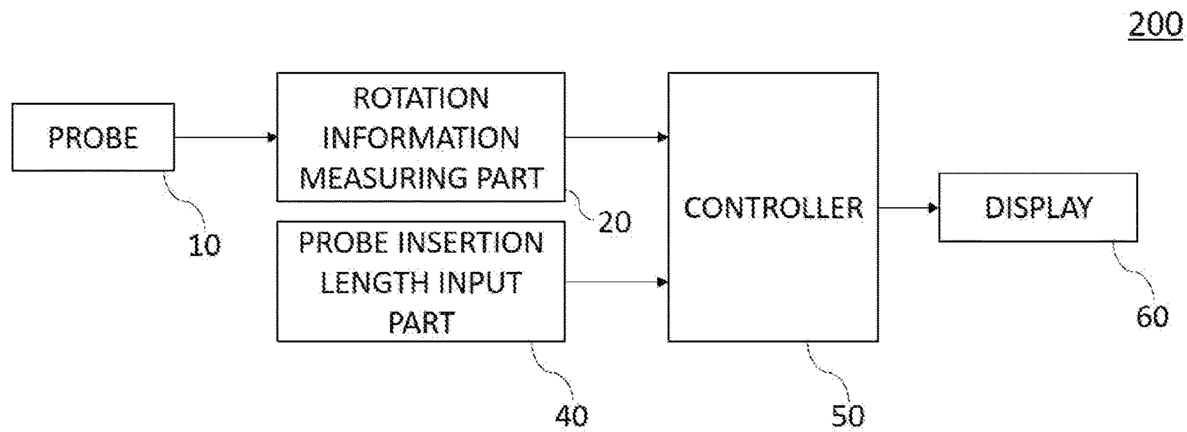
FIG. 7 is a block diagram showing a flexible portion shape estimating device according to a second embodiment of the present disclosure.

FIG. 7 is a block diagram showing a flexible portion shape estimating device according to a second embodiment of the present disclosure. As shown in FIG. 7, the flexible portion shape estimating device 200 according to the second embodiment of the present disclosure includes a probe 10 and a rotation information measuring part 20. According to the present disclosure, further, the flexible portion shape estimating device 200 includes a probe insertion length input part 40, a controller 50, and a display 60.

The flexible portion shape estimating device 200 according to the second embodiment of the present disclosure as shown in FIG. 7 is similar to the flexible portion shape estimating device 100 according to the first embodiment of the present disclosure as shown in FIG. 2, except that the probe insertion length input part 40 is provided, instead of the probe insertion length measuring part 30.

The probe 10 is inserted into the flexible portion 73 of the endoscope device as shown in FIG. 1. The probe 10 includes the torque transmission wire 13 for transmitting a torque applied to one end thereof to the other end thereof. The rotation information measuring part 20 is coupled to the other end of the probe 10 to measure rotation information on the other end of the torque transmission wire 13. The other end of the torque transmission wire 13 disposed in the wire channel 15 of the interior of the outer tubular body 11 is connected to the rotation information measuring part 20. The probe 10 and the rotation information measuring part 20 have been already explained with reference to FIGS. 2 to 6, and therefore, a detailed explanation on them will be avoided for the brevity of the description.

The probe insertion length input part 40 receives a probe insertion length from the user, which is the inserted length of the probe 10 into the flexible portion 73 after passing through the inserting part 85 of endoscope treatment. When the probe 10 is inserted into the flexible portion 73 through the endoscope treatment instrument inserting part 85, the inserted length of the probe 10 is observed by the user so that the probe insertion length is inputted through the probe insertion length input part 40 by the user. For example, the probe insertion length input part 40 has a shape of a pedal, and in this case, the probe insertion length is inputted according to at least one of the number of times the pedal is stepped and the pedal stepping interval. Whenever the probe 10 is inserted by given length (e.g. 10 cm) into the flexible portion 73, for example, the probe insertion length input part 40 having the shape of the pedal is stepped by the user. The input signal from the probe insertion length input part 40 is transmitted to the controller 50.

According to the present disclosure, the probe 10 may have probe length markers indicated at given intervals on the outer peripheral surface thereof, and the length of the probe 10 inserted into the flexible portion 73 is recognized by the user through the probe length markers to allow the probe insertion length input part 40 to be manipulated by the user. According to the present disclosure, in addition to the pedal type input means, the probe insertion length input part 40 is freely selected from a toggle switch, a keypad for directly inputting the probe insertion length with numbers, and other input means for inputting the probe insertion length. According to the present disclosure, if the probe 10 moves backwards inside the flexible portion 73, a backward moving signal, not forward moving signal, is inputted by the user through the probe insertion length input part 40, so that the probe insertion length is decreased.

The controller 50 analyzes the rotation information on the other end of the torque transmission wire 13 received from the rotation information measuring part 20 and the probe insertion length received from the probe insertion length input part 40 to estimate the shape of the flexible portion 73 into which the probe 10 is inserted. The controller 50 recognizes the probe insertion length at the time point when a signal is inputted through the signal inputted from the probe insertion length input part 40 and allows the recognized probe insertion length to correspond to the rotation information on the other end of the torque transmission wire 13, thereby estimating the shape of the probe 10 and the shape of the flexible portion 73 into which the probe 10 is inserted. If the controller 50 analyzes the signals inputted sequentially from the probe insertion length input part 40 to allow the corresponding probe insertion length to correspond to the rotation information on the other end of the torque transmission wire 13, the whole shape of the flexible portion 73 into which the probe 10 is inserted can be estimated. According to the present disclosure, the controller 50 may analyze the rotation information on the other end of the torque transmission wire 13 received from the rotation information measuring part 20 to estimate the shape of the flexible portion 73 into which the probe 10 is inserted. In this case, the probe insertion length input part 40 may be omitted.

The display 60 receives the information on the estimated shape of the flexible portion 73 from the controller 50 and displays the estimated shape of the flexible portion 73 to the user.

On the other hand, the flexible portion shape estimating device 200 according to the second embodiment of the present disclosure includes both of the probe insertion length measuring part 30 and the probe insertion length input part 40, and otherwise, the flexible portion shape estimating device 200 includes any one of the probe insertion length measuring part 30 and the probe insertion length input part 40 according to the user's selection.

Figure 8:
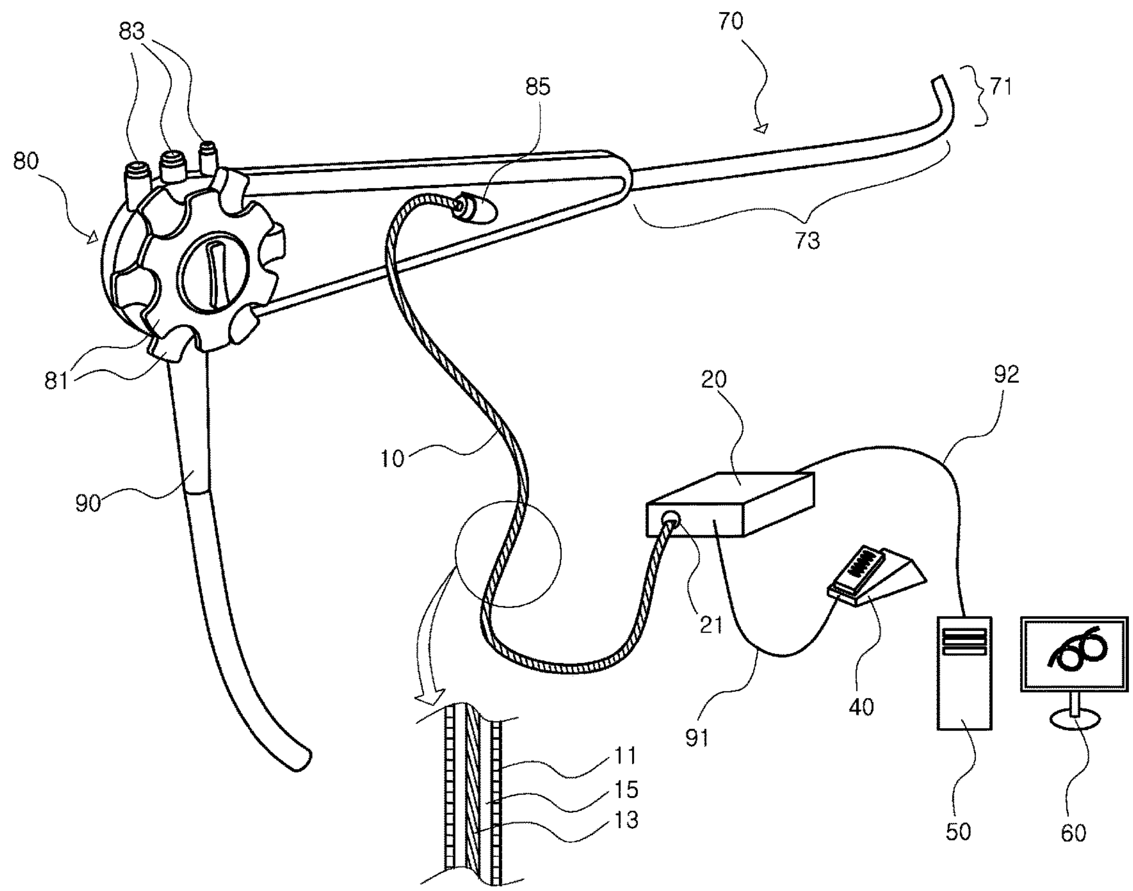
FIG. 8 is a perspective view showing an in-use state of the flexible portion shape estimating device according to the second embodiment of the present disclosure.

FIG. 8 is a perspective view showing an in-use state of the flexible portion shape estimating device according to the second embodiment of the present disclosure. The flexible portion shape estimating device 200 as shown in FIG. 7 may be implemented as shown in FIG. 8. As shown in FIG. 8, the flexible portion shape estimating device 200 according to the second embodiment of the present disclosure includes the probe 10, the rotation information measuring part 20, the probe insertion length input part 40, the controller 50, and the display 60.

The probe 10 has the shape of the tubular body in such a manner as to be inserted into the endoscope treatment instrument inserting part 85. Also, the probe 10 is connected to the rotation information measuring part 20. The probe 10 includes the outer tubular body 11, the torque transmission wire 13, and the wire channel 15. The outer tubular body 11 includes the wire channel 15 formed in the interior thereof. The torque transmission wire 13 is disposed in the wire channel 15 inside the outer tubular body 11. The detailed characteristics of the probe 10 and the shape of the probe 10 inserted into the flexible portion 73 are similar to those as mentioned above with reference to FIGS. 3 to 6, and therefore, a detailed explanation on them will be avoided for the brevity of the description.

The rotation information measuring part 20 is coupled to the other end of the probe 10 to measure the rotation information on the other end of the torque transmission wire 13. The rotation information measuring part 20 is connected to the probe 10 through a probe coupling part 21. For example, the other end of the torque transmission wire 13 of the probe 10 passes through the probe coupling part 21 and is thus disposed inside the rotation information measuring part 20. The other end of the torque transmission wire 13 is disposed on a position adjacent to the torque sensor or the rotation angle sensor of the rotation information measuring part 20. The rotation information measuring part 20 measures the torque generated by the torque transmission wire 13 or measures the rotation angle of the torque transmission wire 13 generated from the torque. The rotation information measuring part 20 and the controller 50 are connected to each other by means of a communication line 92 to transmit and receive data to and from each other.

The probe insertion length input part 40 may receive the probe insertion length from the user, which is the inserted length of the probe 10 into the flexible portion 73 after passing through the inserting part 85 of the endoscope treatment instrument. As shown in FIG. 8, the probe insertion length input part 40 has a shape of a pedal, and in this case, the probe insertion length is inputted according to at least one of the number of times the pedal is stepped on and the pedal stepping interval. The input signal from the probe insertion length input part 40 is transmitted to the controller 50. The rotation information measuring part 20 and the probe insertion length input part 40 are connected to each other by means of a communication line 91 to transmit and receive data to and from each other. For example, the probe insertion length input part 40 is disposed around the rotation information measuring part 20.

According to the present disclosure, the probe insertion length input part 40 may have a shape of a toggle switch. In this case, the probe insertion length input part 40 implemented by the toggle switch is pressed to input the probe insertion length. Whenever the probe 10 is inserted by given length (e.g. 10 cm) into the flexible portion 73, for example, the toggle switch is pressed. The input signal through the toggle switch is transmitted to the controller 50.

The controller 50 analyzes the rotation information on the other end of the torque transmission wire 13 received from the rotation information measuring part 20 and the probe insertion length received from the probe insertion length input part 40 to estimate the shape of the flexible portion 73 into which the probe 10 is inserted. The controller 50 analyzes at least one of the torque and the rotation angle on the other end of the torque transmission wire 13 to obtain the rotation information on the other end of the torque transmission wire 13.

The controller 50 recognizes the probe insertion length at the time point when a signal is inputted through the signal inputted from the probe insertion length input part 40 and allows the recognized probe insertion length to correspond to the rotation information on the other end of the torque transmission wire 13, thereby estimating the shape of the probe 10 and the shape of the flexible portion 73 into which the probe 10 is inserted. If the controller 50 analyzes the signals inputted sequentially from the probe insertion length input part 40 to allow the corresponding probe insertion length to correspond to the rotation information on the other end of the torque transmission wire 13, the whole shape of the flexible portion 73 into which the probe 10 is inserted can be estimated. The controller 50 measures the changes in the torque or rotation angle of the torque transmission wire 13 at respective time points wherein the signals are inputted from the probe insertion length input part 40.

The display 60 receives the information on the estimated shape of the flexible portion 73 from the controller 50 and displays the estimated shape of the flexible portion 73 to the user. The display 60 displays screens according to the display signals received from the controller 50 and provides the screens to the user.

Figure 9:
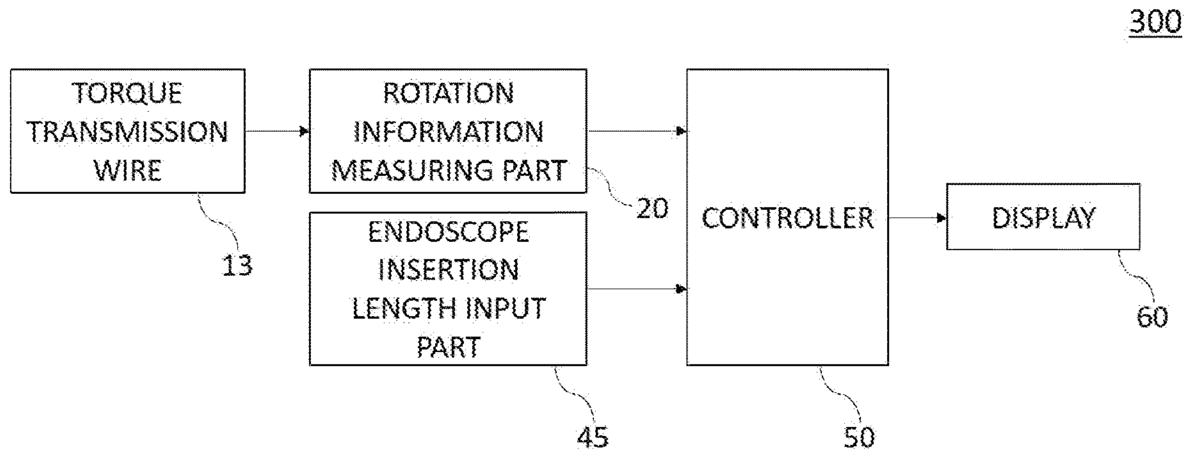
FIG. 9 is a block diagram showing an endoscope system having a flexible portion shape estimating device according to a first embodiment of the present disclosure.

FIG. 9 is a block diagram showing an endoscope system having a flexible portion shape estimating device according to the first embodiment of the present disclosure. As shown in FIG. 9, an endoscope system 300 having a flexible portion shape estimating device according to the present disclosure includes a torque transmission wire 13 and a rotation information measuring part 20. According to the present disclosure, furthermore, the endoscope system 300 includes an endoscope insertion length input part 45, a controller 50, and a display 60. The explanation given with reference to FIGS. 1 to 8 is applied similarly to the endoscope system 300 within the range where it does not conflict with the characteristics of the endoscope system 300.

The torque transmission wire 13 is inserted into a flexible portion 73. The flexible portion 73 is bendable by means of an external force and has a wire channel 75 formed at the interior thereof. The torque transmission wire 13 is disposed in the wire channel 75 and transmits the torque applied to one end thereof to the other end thereof.

The rotation information measuring part 20 is coupled to the other end of the torque transmission wire 13 to measure rotation information on the other end of the torque transmission wire 13. The rotation information measuring part 20 includes at least one of the torque sensors for measuring a torque on the other end of the torque transmission wire 13 and a rotation angle sensor for measuring the rotation angle on the other end of the torque transmission wire 13.

The endoscope insertion length input part 45 receives, from a user, an endoscope insertion length as an insertion length of an endoscope inserting part 70 having the flexible portion 73 into the patient's body. For example, the endoscope insertion length input part 45 has a shape of a pedal, and in this case, the endoscope insertion length is inputted according to at least one of the number of times the pedal is stepped on and a pedal stepping interval. According to the present disclosure, the endoscope insertion length input part 45 is similar to the probe insertion length input part 40, and otherwise, it may be freely changed.

The controller 50 analyzes the rotation information on the other end of the torque transmission wire 13 received from the rotation information measuring part 20 and the endoscope insertion length received from the endoscope insertion length input part 45 to estimate the shape of the flexible portion 73. According to the present disclosure, the controller 50 may analyze the rotation information on the other end of the torque transmission wire 13 received from the rotation information measuring part 20 to estimate the shape of the flexible portion 73 into which the torque transmission wire 13 is inserted. In this case, the endoscope insertion length input part 45 may be omitted.

The display 60 receives the information on the estimated shape of the flexible portion 73 from the controller 50 and displays the estimated shape of the flexible portion 73 to the user.

Figure 10:
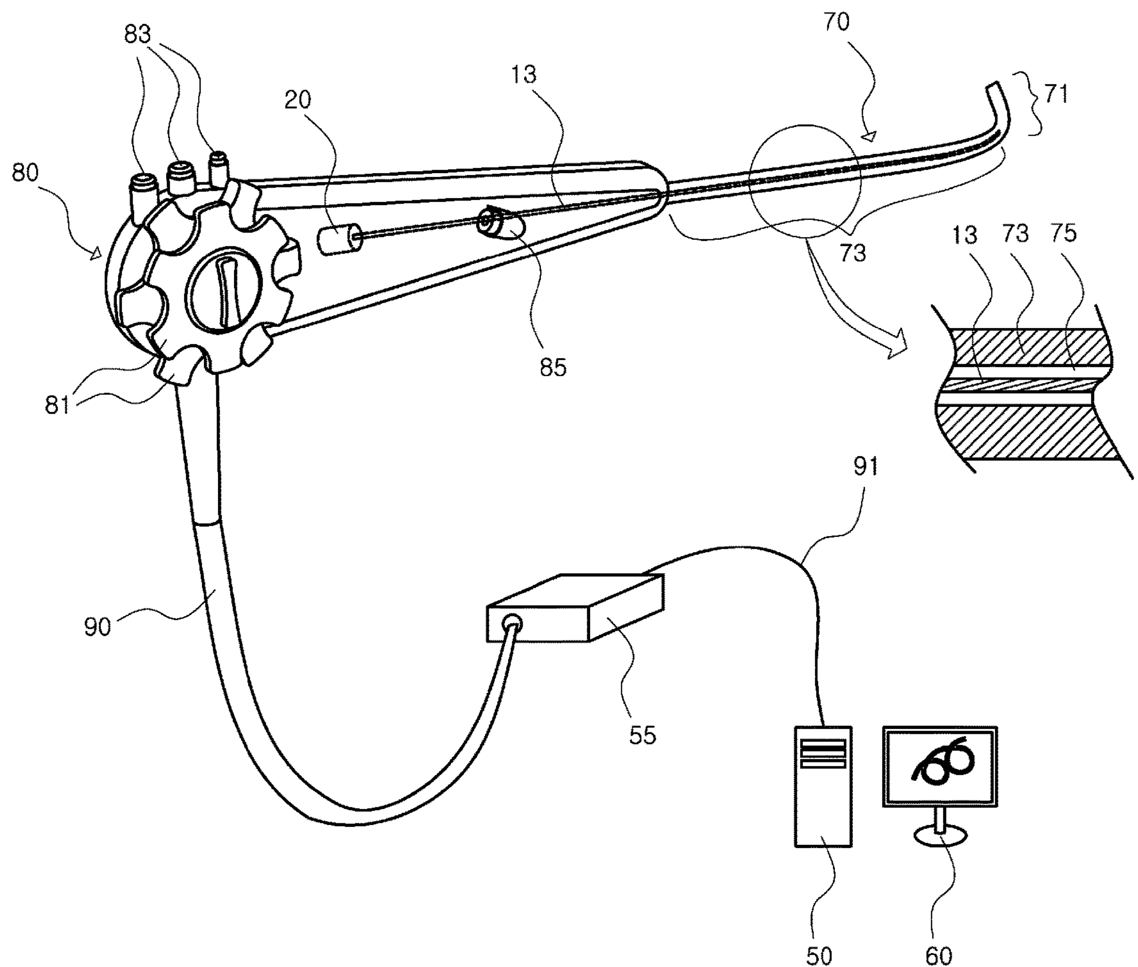
FIG. 10 is a perspective view showing the endoscope system having the flexible portion shape estimating device according to the first embodiment of the present disclosure.

FIG. 10 is a perspective view showing the endoscope system having the flexible portion shape estimating device according to the first embodiment of the present disclosure. The endoscope system 300 having the flexible portion shape estimating device according to the first embodiment of the present disclosure as shown in FIG. 9 may be implemented as shown in FIG. 10. As shown in FIG. 10, the endoscope system 300 having the flexible portion shape estimating device according to the first embodiment of the present disclosure includes the endoscope inserting part 70 and the endoscope operating part 80. According to the present disclosure, the endoscope system 300 further includes the controller 50, the endoscope monitoring device 55, the display 60, and the universal cord 90.

The endoscope inserting part 70 is coupled to one area of the endoscope operating part 80 and is also inserted into a subject's body. The endoscope inserting part 70 includes a freely bendable portion 71 and the flexible portion 73 having flexibility in such a manner as to be easily bent and returned to its original shape by means of an external force. The flexible portion 73 has the wire channel 75 formed at the interior thereof. The wire channel 75 is a separate channel from the endoscope treatment instrument channel 74 which is formed inside of the endoscope inserting part 70 in such a manner to communicate with the endoscope treatment instrument inserting part 85. Even if not shown in FIG. 10, the endoscope treatment instrument channel 74 is formed inside of the endoscope inserting part 70 in such a manner to communicate with the endoscope treatment instrument inserting part 85. Furthermore, parts like an observing window, a light window, a treatment instrument insertion channel opening, an air transmitting nozzle, and a water transmitting nozzle may be disposed on one area of the bendable portion 71.

As shown in FIG. 10, the torque transmission wire 13 is inserted into the flexible portion 73. The torque transmission wire 13 is disposed in the wire channel 75 and transmits the torque applied to one end thereof to the other end thereof. The other end of the torque transmission wire 13 is connected to the rotation information measuring part 20.

The rotation information measuring part 20 is coupled to the other end of the torque transmission wire 13 to measure rotation information on the other end of the torque transmission wire 13. The rotation information measuring part 20 is disposed inside the endoscope operating part 80. The rotation information measuring part 20 includes at least one of the torque sensors for measuring the torque on the other end of the torque transmission wire 13 and the rotation angle sensor for measuring the rotation angle on the other end of the torque transmission wire 13. The other end of the torque transmission wire 13 is disposed on a position adjacent to the torque sensor or the rotation angle sensor of the rotation information measuring part 20. The rotation information measuring part 20 transmits the rotation information on the other end of the torque transmission wire 13 to the endoscope monitoring device 55 and the controller 50 through the universal cord 90.

The endoscope operating part 80 is disposed between the endoscope inserting part 70 and the universal cord 90. The endoscope operating part 80 includes the bent operating levers 81 and the operating switch part 83, and furthermore, it includes an endoscope treatment instrument inserting part 85 disposed on the side surface thereof.

The endoscope insertion length input part 45 (See FIG. 9) receives, the endoscope insertion length from the user which is the inserted length of the endoscope inserting part 70 having the flexible portion 73 into the patient's body. The length of the endoscope inserting part 70 inserted into the patient's body is recognized by the user so that the endoscope insertion length is inputted through the endoscope insertion length input part 45. The endoscope insertion length input part 45 is disposed on the bent operating levers 81 or the operating switch part 83. The endoscope insertion length input part 45 has a shape of a toggle switch, and in this case, the endoscope insertion length input part 45 is pressed to input the endoscope insertion length. Whenever the endoscope inserting part 70 is inserted by given length (e.g. 10 cm) into the patient's body, for example, the toggle switch is pressed. The input signal through the toggle switch is transmitted to the endoscope monitoring device 55 and the controller 50 through the universal cord 90 and the communication line 91.

According to the present disclosure, the endoscope inserting part 70 may have endoscope length markers indicated at given intervals on the outer peripheral surface thereof, and the length of the endoscope inserting part 70 inserted into the patient's body is recognized by the user through the endoscope length markers to allow the endoscope insertion length input part 45 to be manipulated by the user.

According to the present disclosure, as shown in FIG. 8, the endoscope insertion length input part 45 has a shape of a pedal, and in this case, the endoscope insertion length is inputted according to at least one of the number of times the pedal is stepped on and the pedal stepping interval. According to the present disclosure, in addition to the pedal type input means and the toggle switch, the endoscope insertion length input part 45 may be freely selected from a keypad for directly inputting the endoscope insertion length with numbers, and other input means for inputting the endoscope insertion length. According to the present disclosure, if the endoscope inserting part 70 moves backward inside the patient's body, a backward moving signal, not forward moving signal, is inputted by the user through the endoscope insertion length input part 45, so that the endoscope insertion length is decreased.

The universal cord 90 is coupled to one area of the endoscope operating part 80 and includes a transmission cord for a camera or a light source unit of the endoscope, an air transmission tube, a water transmission tube, and a suction tube, disposed in the interior thereof. The transmission cord, the air transmission tube, the water transmission tube, and the suction tube pass through the interior of the endoscope operating part 80 in such a manner as to be extended to the endoscope inserting part 70. The endoscope inserting part 70 has a channel formed therein to pass the transmission cord, the air transmission tube, the water transmission tube, and the suction tube therethrough. The other end of the universal cord 90 is connected to the endoscope monitoring device 55.

The endoscope monitoring device 55 serves to monitor electromagnetic states of the endoscope, the light source unit, the air transmission tube, the water transmission tube, and the suction tube. The endoscope monitoring device 55 is connected to the controller 50 through the communication line 91. The information on the endoscope monitored by means of the endoscope monitoring device 55 is provided to the user through the display 60. According to the present disclosure, the endoscope monitoring device 55 may be omitted.

The controller 50 analyzes the rotation information on the other end of the torque transmission wire 13 received from the rotation information measuring part 20 and the endoscope insertion length received from the endoscope insertion length input part 45 to estimate the shape of the flexible portion 73 into which the torque transmission wire 13 is inserted. The controller 50 analyzes at least one of the torque and the rotation angle on the other end of the torque transmission wire 13 to obtain the rotation information on the other end of the torque transmission wire 13.

The controller 50 recognizes the endoscope insertion length at the time point when a signal is inputted through the signal inputted from the endoscope insertion length input part 45 and allows the recognized endoscope insertion length to correspond to the rotation information on the other end of the torque transmission wire 13, thereby estimating the shape of the torque transmission wire 13 and the shape of the flexible portion 73 into which the torque transmission wire 13 is inserted. If the controller 50 analyzes the signals inputted sequentially from the endoscope insertion length input part 45 to allow the corresponding endoscope insertion length to correspond to the rotation information on the other end of the torque transmission wire 13, the whole shape of the flexible portion 73 into which the torque transmission wire 13 is inserted can be estimated. The controller 50 measures the changes in the torque or rotation angle of the torque transmission wire 13 at respective time points wherein the signals are inputted from the endoscope insertion length input part 45.

According to the present disclosure, the controller 50 may analyze the rotation information on the other end of the torque transmission wire 13 received from the rotation information measuring part 20 to estimate the shape of the flexible portion 73 into which the torque transmission wire 13 is inserted. In this case, the endoscope insertion length input part 45 may be omitted.

The display 60 receives the information on the estimated shape of the flexible portion 73 from the controller 50 and displays the estimated shape of the flexible portion 73 to the user. The display 60 displays screens according to the display signals received from the controller 50 and provides the screens to the user.

On the other hand, as shown in FIG. 10, the endoscope monitoring device 55, the controller 50, and the display 60 are separated from each other, but of course, they may be integrated into one body. Furthermore, the communication line 91 may be changed or removed, and according to the present disclosure, the endoscope monitoring device 55 and the controller 50 can transmit and receive data to and from each other by means of wireless communication.

The endoscope system 300 having the flexible portion shape estimating device according to the present disclosure, as shown in FIG. 10, is configured to insert the torque transmission wire 13 into the wire channel 75 formed inside the endoscope inserting part 70 and to fix the torque transmission wire 13 to the front-end periphery of the flexible portion 73.

While the flexible portion 73 is moving to the subject's body, if resistance occurs in the moving direction to the flexible portion 73, a major axis of the flexible portion 73 is bent like a spring coil, and therefore, a portion of elastic energy generated from the resistance generates a torque around the major axis of the flexible portion 73. Through the generation of the torque, the flexible portion 73 rotates around the major axis.

One end of the torque transmission wire 13 is fixed to the front-end periphery of the flexible portion 73, and thus, the torque generated by the bending or twisting of the flexible portion 73 is transmitted to the rotation information measuring part 20 through the torque transmission wire 13. The rotation information measuring part 20 measures the torque or rotation angle on the other end of the torque transmission wire 13. The rotation information on the other end of the torque transmission wire 13, which is measured by the rotation information measuring part 20, is transmitted to at least one of the endoscope monitoring device 55 and the controller 50 through the universal cord 90, and at least one of the endoscope monitoring device 55 and the controller 50 estimates the changes in the shape of the flexible portion 73 caused by the bending or twisting of the flexible portion 73.

While the flexible portion 73 of the endoscope inserting part 70 is moving to the direction of the major axis of the endoscope, if the front-end periphery of the flexible portion 73 does not move, a given portion of the flexible portion 73 except the front end periphery thereof becomes bent or twisted, and in this case, it is hard to estimate the bent or twisted portion of the flexible portion 73.

If the endoscope insertion length input part 45 (See FIG. 9) is provided on the operating switch part 83 of the endoscope operating part 80, a moment before the endoscope inserting part 70 moves forward into the subject's body and a moment after it moves by a given distance are transmitted to the rotation information measuring part 20 through the endoscope insertion length input part 45. Accordingly, the rotation information measuring part 20 can measure the changes in the rotation angles of the torque transmission wire 13 the moment before the endoscope inserting part 70 moves forward in the subject's body and the moment after it moves by the given distance.

The rotation information of the torque transmission wire 13 obtained from the twist of the flexible portion 73 and the moving distance of the flexible portion 73 in the subject's body have a consistent relationship with the changes in the shape of the flexible portion 73. In detail, as a change in the torque transmitted to the torque transmission wire 13 per a unit moving distance of the flexible portion 73 in the subject's body or a change in the rotation angle by the rotation of the torque transmission wire 13 per the unit moving distance of the flexible portion 73 in the subject's body is increased, the degree of twist of the flexible portion 73 is increased.

Through the changes in the torque or rotation angle, therefore, the controller 50 estimates the changes in the shape of the flexible portion 73 caused by the bending or twisting of the flexible portion 73. With the changes in the rotation angle of the torque transmission wire 13, the controller 50 estimates the degree of twist of the flexible portion 73 according to the unit moving distance of the front-end periphery of the flexible portion 73. The controller 50 provides the estimated shape of the flexible portion 73 to the user through the display 60.

According to the present disclosure, on the other hand, the endoscope system 300 further may include a metal bar (not shown) coupled to the other end of the torque transmission wire 13. The metal bar is connected to the rotation information measuring part 20, and the rotation information measuring part 20 measures at least one of the rotation angles and the torque of the metal bar to measure the rotation information on the other end of the torque transmission wire 13. If it is difficult to directly measure the rotation information on the other end of the torque transmission wire 13, the rotation information of the metal bar coupled to the other end of the torque transmission wire 13 is measured so that the rotation information on the other end of the torque transmission wire 13 can be indirectly measured.

According to the present disclosure, on the other hand, the endoscope system 300 having the flexible portion shape estimating device according to the present disclosure further includes an endoscope insertion length measuring part (not shown) connected to the endoscope inserting part 70 to measure an insertion length of the endoscope inserting part 70 when the endoscope inserting part 70 moves to the subject's body. For example, the endoscope insertion length measuring part is disposed around the endoscope inserting part 70 inserted into the subject's body or around the patient's body into which the endoscope inserting part 70 is inserted. The endoscope insertion length measuring part measures an endoscope insertion length as an insertion length of the endoscope inserting part 70 into the patient's body. According to the present disclosure, in a similar manner as the probe insertion length measuring part 30, the endoscope insertion length measuring part can be implemented by a rotation type roller, a laser, and an ultrasonic wave.

According to the present disclosure, the endoscope insertion length measuring part includes a plurality of pressure sensors (not shown) spaced apart from each other by a given distance on the outer peripheral surface of the endoscope inserting part 70. For example, the plurality of pressure sensors is spaced apart from each other at 10 cm intervals on the outer peripheral surface of the endoscope inserting part 70. The plurality of pressure sensors senses pressure differences generated at the time when the endoscope inserting part 70 moves to the interior (for example, the anus) of the patient's body and transmit the sensed signals to the controller 50. The controller 50 analyzes a degree of insertion of the endoscope inserting part 70 into the patient's body through the sensing signals received from the plurality of pressure sensors. Accordingly, the endoscope insertion length measuring part can measure the endoscope insertion length as the insertion length of the endoscope inserting part 70 into the patient's body.

According to the present disclosure, furthermore, the endoscope insertion length measuring part includes a temperature sensor (not shown) disposed on one area of the endoscope inserting part 70. For example, the temperature sensor is disposed on the outer peripheral surface of the bendable portion 71 of the endoscope inserting part 70 or on the outer peripheral surface of the front-end periphery of the flexible portion 73. If the endoscope inserting part 70 is inserted into the patient's body, a temperature on the outer peripheral surface of the endoscope inserting part 70 becomes raised by means of a body temperature of the patient, and through the principle as mentioned above, accordingly, the temperature sensor senses the temperature on the outer peripheral surface of the endoscope inserting part 70. The temperature information sensed by the temperature sensor is transmitted to the controller 50. It is determined through the controller 50 that as the temperature sensor sensed the rise of body temperature, the endoscope inserting part 70 is gradually deeply inserted into the patient's body, and accordingly, the endoscope insertion length measuring part can measure the endoscope insertion length.

According to the present disclosure, furthermore, the endoscope insertion length measuring part may be connected wiredly or wirelessly to the controller 50. The endoscope insertion length measuring part is attached to one area of the patient's body to measure the endoscope insertion length. The controller 50 analyzes the rotation information on the other end of the torque transmission wire 13 received from the rotation information measuring part 20 and the endoscope insertion length received from the endoscope insertion length measuring part to estimate the shape of the flexible portion 73.

According to the present disclosure, the endoscope system 300 having the flexible portion shape estimating device according to the present disclosure includes both of the endoscope insertion length measuring part and the endoscope insertion length input part 45, and the user can use either the endoscope insertion length measuring part and the endoscope insertion length input part 45 according to the selection.

Figure 11:
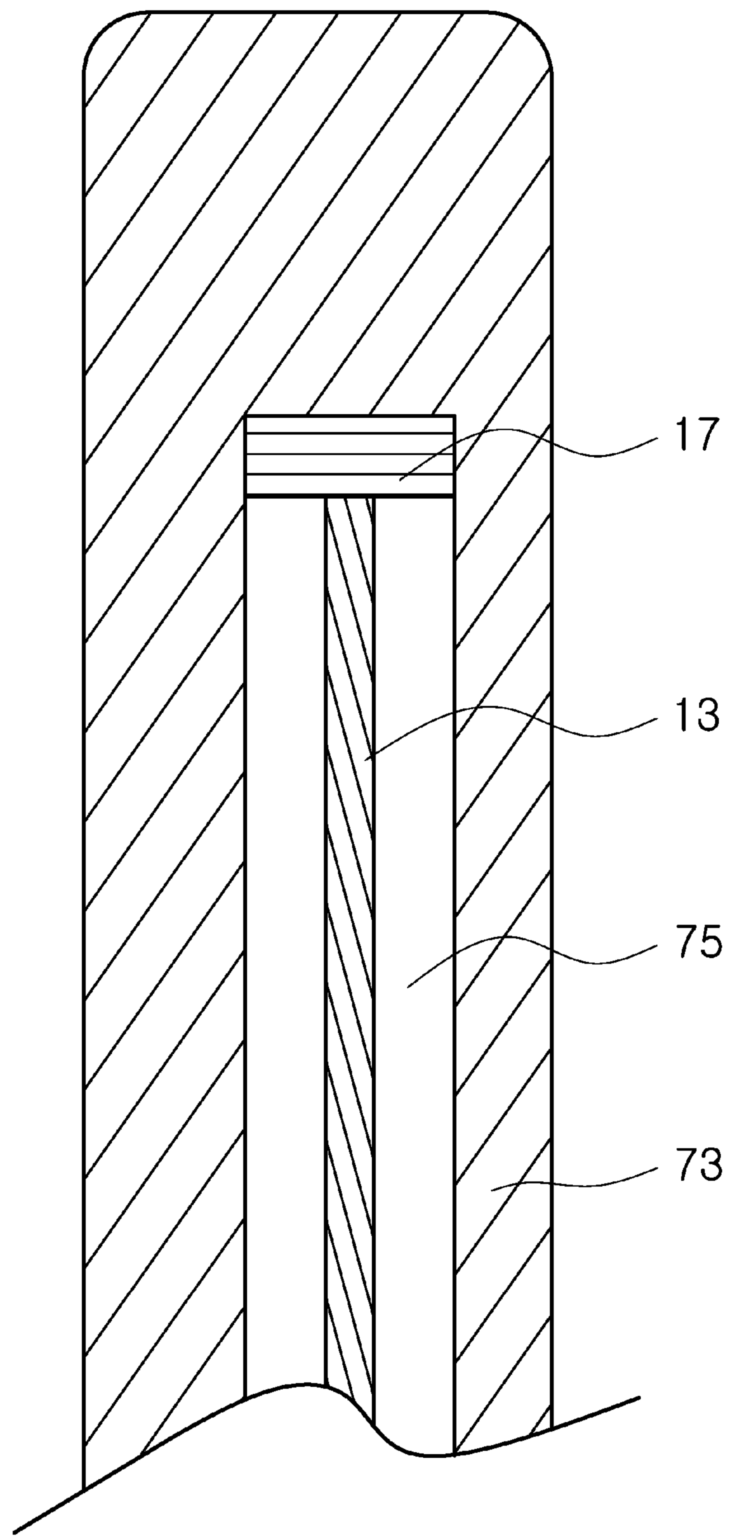
FIG. 11 is a sectional view showing a flexible portion of the endoscope system having the flexible portion shape estimating device according to the first embodiment of the present disclosure.

FIG. 11 is a sectional view showing the flexible portion of the endoscope system having the flexible portion shape estimating device according to the first embodiment of the present disclosure. FIG. 11 shows the front-end periphery of the flexible portion 73 of the endoscope system 300. Even if not shown in FIG. 11, the bendable portion 71 is formed on one end of the flexible portion 73 as shown in FIG. 10.

Referring to FIG. 11, the wire channel 75 is formed in the interior of the flexible portion 73 having the shape of the tubular body. For example, the wire channel 15 may be empty.

The torque transmission wire 13 is inserted into the flexible portion 73 and is then disposed in the wire channel 75. One area of the torque transmission wire 13 is fixedly coupled to the inner peripheral surface of the flexible portion 73. The torque transmission wire 13 is inserted toward the front-end periphery of the flexible portion 73 and is then fixedly coupled to the flexible portion 73 around the front end of the flexible portion 73.

As shown in FIG. 11, a wire fixing member 17 is formed along the front-end inner periphery of the flexible portion 73, and by means of the wire fixing member 17, the torque transmission wire 13 is fixed to the inner peripheral surface of the flexible portion 73. Only if the wire fixing member 17 fixedly couples the torque transmission wire 13 to the flexible portion 73, it can be freely changed to various coupling means.

According to the present disclosure, a lubricant may be accommodated in the wire channel 75 to reduce a frictional force between the inner peripheral surface of the flexible portion 73 and the torque transmission wire 13. Through the lubricant, the torque transmission wire 13 does not come into contact with the inner peripheral surface of the flexible portion 73, and otherwise, the frictional force between the inner peripheral surface of the flexible portion 73 and the torque transmission wire 13 is reduced, so that the torque generated from one end of the torque transmission wire 13 is accurately transmitted to the other end of the torque transmission wire 13, without any loss in the middle of the torque transmission wire 13.

According to the present disclosure, further, a material for reducing a frictional force may be coated onto the outer peripheral surface of the torque transmission wire 13 so as to reduce the frictional force between the inner peripheral surface of the flexible portion 73 and the torque transmission wire 13. For example, the material for reducing the frictional force is polytetrafluoroethylene (PTFE), and of course, it may be changed to various materials.

Figure 12:
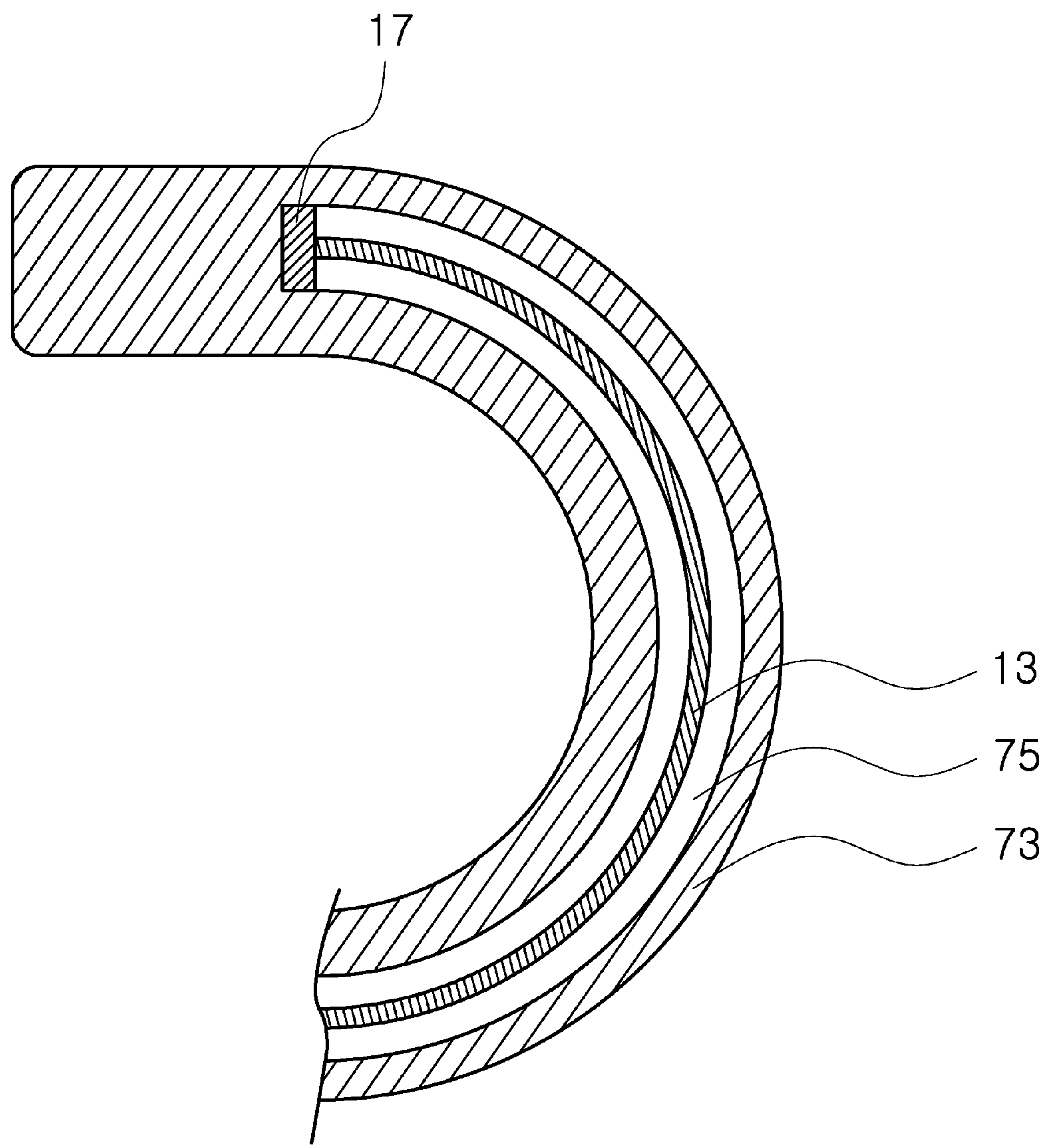
FIG. 12 is a sectional view showing a bent state of the flexible portion of the endoscope system having the flexible portion shape estimating device according to the first embodiment of the present disclosure.

FIG. 12 is a sectional view showing a bent state of the flexible portion of the endoscope system having the flexible portion shape estimating device according to the first embodiment of the present disclosure. In detail, FIG. 12 shows one end of the torque transmission wire 13 fixed to the inner peripheral surface of the flexible portion 73 by means of the wire fixing member 17 and the torque transmission wire 13 bent in the same manner as the flexible portion 73 according to the bending of the flexible portion 73.

If the flexible portion 73 is bent or twisted, while the endoscope inserting part 70 is being inserted into the subject's body, the rotation force generated from the front-end periphery of the flexible portion 73 around the wire fixing member 17 is transmitted to the rotation information measuring part 20 through the torque transmission wire 13.

The controller 50 analyzes the rotation information on the other end of the torque transmission wire 13 received from the rotation information measuring part 20 and the endoscope insertion length received from the endoscope insertion length input part 45 to estimate the shape of the flexible portion 73. The display 60 receives the information on the estimated shape of the flexible portion 73 from the controller 50 and displays the estimated shape of the flexible portion 73 to the user.

Figure 13:
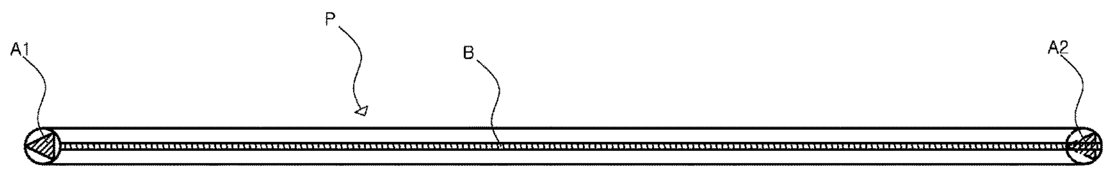
FIGS. 13 to 15 show the shape change estimation principle of the flexible portion according to the embodiment of the present disclosure.
Figure 14:
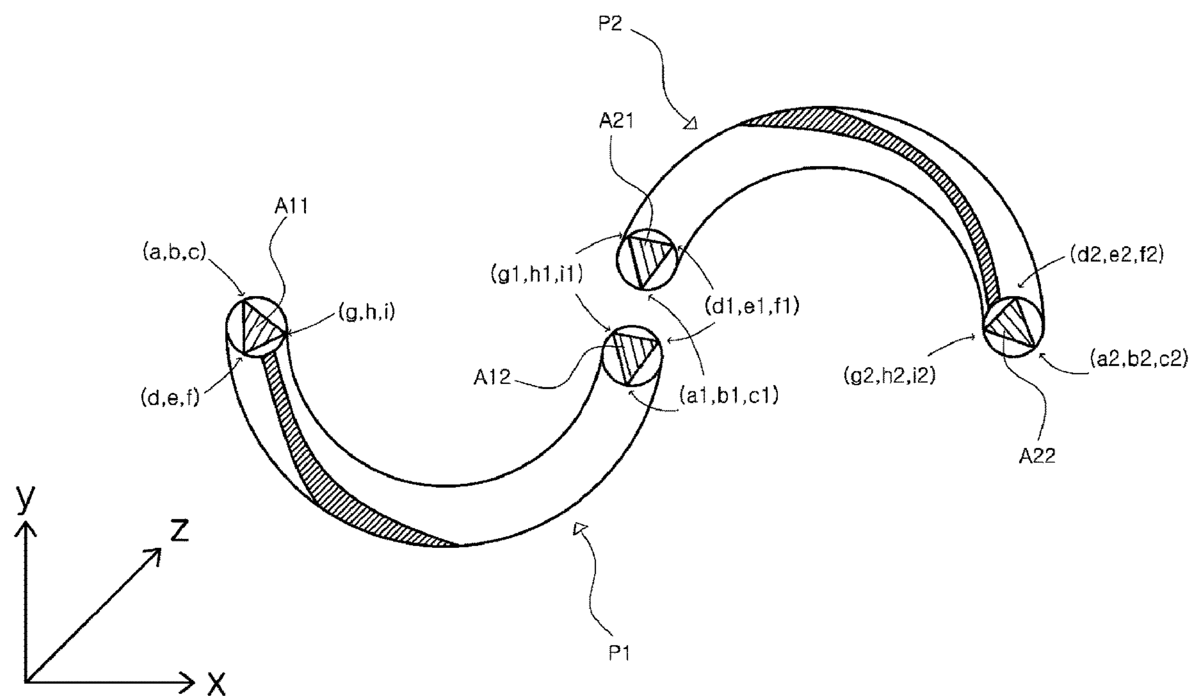
Figure 15:
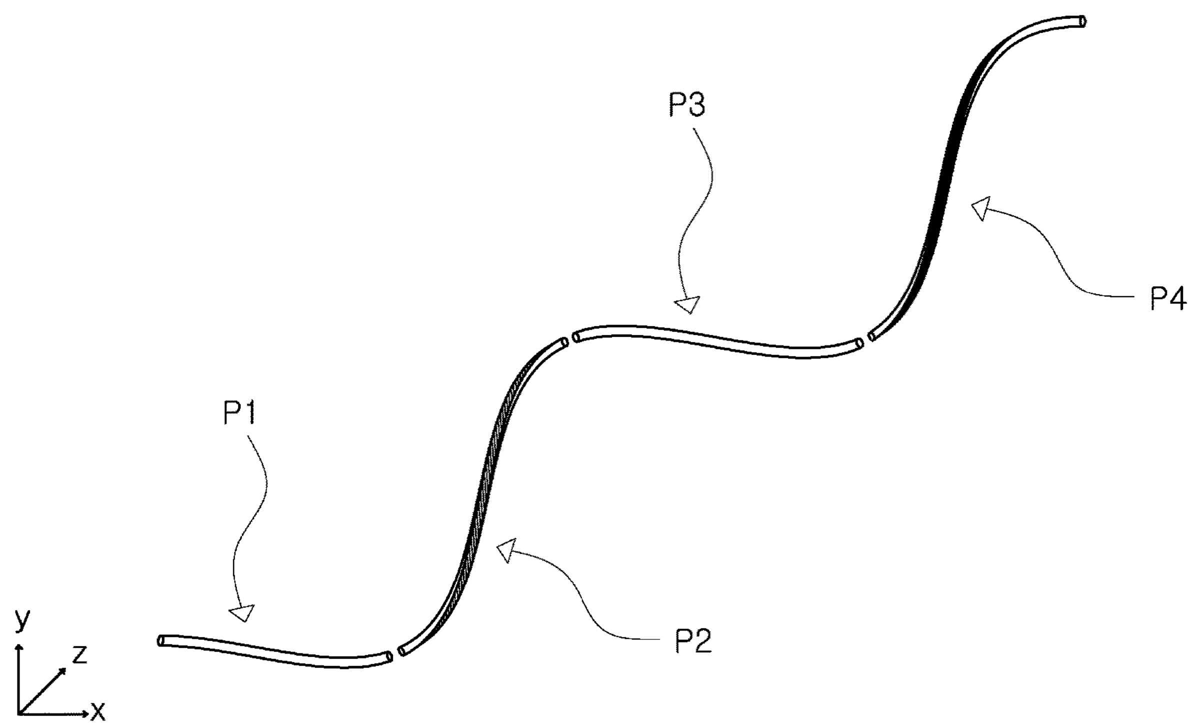

FIGS. 13 to 15 show the shape change estimation principle of the flexible portion according to the embodiment of the present disclosure.

As shown in FIG. 13, a flexible portion model P is shown to explain the shape change estimation principle of the flexible portion according to the embodiment of the present disclosure. The flexible portion model P has a bendable linear shape like an endoscope. FIG. 13 shows the case where the flexible portion model P is not bent or twisted.

The flexible portion model P may have given polygonal (for example, triangular) materials contained consistently along the major axis thereof. In detail, the polygonal materials A1 and A2 are indicated on the left and right sectional areas of the flexible portion model P. A marker B for indicating the twist of the flexible portion model P is provided on the outer peripheral surface of the flexible portion model P.

FIG. 14 shows a state where the flexible portion model P rotates one time in a clockwise direction.

The given polygonal materials are contained consistently along the major axis of the flexible portion model P, and even if any position on the section of the flexible portion model P is cut off, accordingly, it can be appreciated that the section of the flexible portion model P has the same pattern having the given polygonal materials.

As shown in FIG. 14, if the section on the intermediate portion of the flexible portion model P is cut off in a state where the flexible portion model P rotates one time in the clockwise direction, two twisted flexible portion models P1 and P2 are provided.

A polygon A11 exposed to the left side of the first flexible portion model P1 has three points on space, and three-dimensional coordinates of the respective points are (a, b, c), (d, e, f), and (g, h, i). Such polygons having the three points on space are contained consistently along the major axes of the flexible portion models P1 and P2, and accordingly, a polygon A12 exposed to the right side of the first flexible portion model P1 has the same shape as the polygon A11 exposed to the left side of the first flexible portion model P1.

Three-dimensional coordinates of the respective points constituting the polygon A12 exposed to the right side of the first flexible portion model P1 are (a1, b1, c1), (d1, e1, f1), and (g1, h1, i1). As shown in FIG. 14, three points constituting a polygon A21 exposed to the left side of the second flexible portion model P2 has the same coordinates on space as the polygon A12 exposed to the right side of the first flexible portion model P1. Three-dimensional coordinates of the respective points constituting a polygon A22 exposed to the right side of the second flexible portion model P2 are (a2, b2, c2), (d2, e2, f2), and (g2, h2, i2).

If the two flexible portion models P1 and P2 are connected to each other to allow the polygon A12 existing on the right side of the first flexible portion model P1 to be arranged correspondingly to the polygon A21 existing on the left side of the second flexible portion model P2 on the same space as each other, the connected shape of the two different flexible portion models P1 and P2 can be shown in a two-dimensional or three-dimensional space.

If the rotation information on the left and right ends of the respective flexible portion models P1 and P2 is measured, degrees of rotation of the flexible portion models P1 and P2 in specific directions can be recognized. Further, if it is assumed that physical properties of the flexible portion models P1 and P2 are the same as each other along the major axes thereof, further, the rotation information on the entire portion of the flexible portion models P1 and P2 except the left and right ends of the flexible portion models P1 and P2 can be estimated using the rotation information on the left and right ends of the flexible portion models P1 and P2. According to the degrees of twist of the flexible portion models P1 and P2, the changes in the shape of the entire flexible portion model P are indicated with a mathematical expression on a three-dimensional surface by means of three-dimensional modeling, so that the flexible portion models P1 and P2 having the different shapes from each other are connected to each other, and they can be displayed in a two-dimensional or three-dimensional space.

The controller 50 can estimate the shape of the probe 10 or the flexible portion 73 according to the probe insertion length or the endoscope insertion length at the moment when the rotation information on the other end of the torque transmission wire 13 is inputted under the above-mentioned principle.

FIG. 15 shows the case where the flexible portion models P1 and P2 having the different shapes from each other are connected to each other and displayed in the two-dimensional or three-dimensional space.

As shown in FIG. 15, a plurality of flexible portion models P1, P2, P3 and P4 are connected to each other, and the rotation information of the respective flexible portion models P1, P2, P3 and P4 is measured to estimate the shape of the entire flexible portion model P.

The display 60 estimates and displays the shape of the flexible portion 73 to the similar shape to the shape of the flexible portion model P as shown in FIG. 15 under the control of the controller 50. The display 60 displays the estimated shape of the flexible portion 73 to a two-dimensional or three-dimensional image.

While the present disclosure has been described with reference to the particular illustrative embodiments, it is not to be restricted by the embodiments but only by the appended claims. It is to be appreciated that those skilled in the art can change or modify the embodiments without departing from the scope and spirit of the present disclosure.

What is claimed is:

1. A device for estimating a shape of a flexible portion, the device comprising:

an endoscope inserting assembly having:

the flexible portion, and an endoscope treatment instrument channel defined inside the endoscope inserting assembly and the flexible portion;

an endoscope operating assembly configured to operate the endoscope inserting assembly and comprising an endoscope treatment instrument inserting assembly;

a probe configured to pass through the endoscope treatment instrument inserting assembly and to be inserted into the flexible portion and slide therein, the probe having:

a torque transmission wire transmitting a torque applied to one end of the torque transmission wire to the other end of the torque transmission wire, and an outer tubular body having a wire channel therein, which accommodates the torque transmission wire;

a rotation information measuring assembly configured to measure rotation information on the other end of the torque transmission wire;

a probe insertion length input part configured to receive a probe insertion length when the probe is inserted into the flexible portion after passing through an inserting part of an endoscope treatment instrument from a user, wherein the one end of the torque transmission wire is fixedly coupled to an inner surface of one end of the outer tubular body, and the other end of the torque transmission wire is located outside the flexible portion and is coupled to the rotation information measuring assembly, wherein the probe comprises a metal bar coupled to the other end of the torque transmission wire, and the metal bar is connected to the rotation information measuring assembly, which is configured to measure at least one of a rotation angle and a torque of the metal bar and is configured to measure the rotation information on the other end of the torque transmission wire, and a controller configured to analyze the probe insertion length and the rotation information on the other end of the torque transmission wire received from the rotation information measuring assembly, and configured to estimate the shape of the flexible portion into which the probe is inserted.

2. The device according to claim 1, wherein a lubricant is accommodated in the wire channel configured to reduce a frictional force between the inner surface of the outer tubular body and the torque transmission wire.

3. The device according to claim 1, wherein the rotation information measuring assembly comprises at least one of a torque sensor configured to measure the torque on the other end of the torque transmission wire and a rotation angle sensor configured to measure a rotation angle on the other end of the torque transmission wire.

4. The device according to claim 1, further comprising:

a display for receiving information on an estimated shape of the flexible portion from the controller to display the estimated shape of the flexible portion to a user.

5. The device according to claim 1, wherein the probe insertion length input part has a shape of a pedal and inputs the probe insertion length according to at least one of a number of times of pedal steps and an interval between the pedal steps.

6. The device according to claim 1, wherein the device comprises:

a display configured to receive information on an estimated shape of the flexible portion from the controller and configured to display the estimated shape of the flexible portion to the user.

7. The device according to claim 1, wherein the probe further comprises a wire fixing member disposed to an inner surface of the one end of the outer tubular body, which is covered, and the coupling the torque transmission wire to the inner surface of the one end of the outer tubular body.

8. The device according to claim 1, wherein the probe has a probe length marker indicated at given intervals on an outer peripheral surface thereof.

9. The device according to claim 1, wherein the endoscope treatment instrument inserting assembly has a through hole into which the endoscope treatment instrument is inserted and communicates with the endoscope treatment instrument channel.

* * * * *